United States Patent [19]

Ksander

[11] Patent Number: 4,939,261

[45] Date of Patent: Jul. 3, 1990

[54] N-SUBSTITUTED BUTYRAMIDE DERIVATIVES USEFUL FOR TREATMENT OF CONDITIONS RESPONSIVE TO INHIBITION OF ENKEPHALINASE

[75] Inventor: Gary M. Ksander, Carmel, N.Y.

[73] Assignee: Ciba-Geigy Corporation, Ardsley, N.Y.

[21] Appl. No.: 98,755

[22] Filed: Sep. 17, 1987

Related U.S. Application Data

[63] Continuation of Ser. No. 772,067, Sep. 3, 1985, abandoned, which is a continuation-in-part of Ser. No. 618,617, Jun. 8, 1984, abandoned.

[30] Foreign Application Priority Data

Jun. 1, 1985 [WO] PCT Int'l Appl. .................. PCT/EP85/00261

[51] Int. Cl.$^5$ .................. C07D 213/55; C07C 101/02; C07C 103/14; A61K 31/44
[52] U.S. Cl. .................. 514/357; 514/332; 514/510; 514/533; 514/563; 546/265; 546/337; 560/39; 560/41; 562/450; 562/444
[58] Field of Search .................. 562/450, 444; 560/41, 560/39; 546/337, 265; 514/357, 332, 563, 510, 533

[56] References Cited

U.S. PATENT DOCUMENTS

| | | | |
|---|---|---|---|
| 4,052,511 | 10/1977 | Cushman et al. | 514/423 |
| 4,105,789 | 8/1978 | Ondetti et al. | 514/563 |
| 4,311,705 | 1/1982 | Ondetti et al. | 514/422 |
| 4,374,847 | 1/1983 | Gruenfeld | 514/415 |
| 4,610,816 | 9/1986 | Berger | 549/452 |

FOREIGN PATENT DOCUMENTS

| | | | |
|---|---|---|---|
| 038758 | 10/1982 | European Pat. Off. | 514/561 |
| 103077 | 3/1984 | European Pat. Off. | 549/454 |
| 110484 | 6/1984 | European Pat. Off. | |

OTHER PUBLICATIONS

Lecouite et al, J. Pharmacology Expermental Therapeutics 237, 937–944 (1986).
Cushman et al Biochemistry 16, 5484 (1977) e.g. p. 5487.
Gruenfeld et al, j. med chem. 26, 1277 (1983).
Llorens et al, Biochem, Biophys, Res. Comm. 96, 1710–6 (1980).
Mumford et al, Biochem. Biophys. Research Comm. 109,1303 (1982).
Roques et al, Life Sciences 31 1749 (1982).
Fournie-Zaluski et al, Life Sciences 31 2947 (1982).

*Primary Examiner*—Alan L. Rotman
*Attorney, Agent, or Firm*—Norbert Gruenfeld

[57] ABSTRACT

Disclosed are compounds of the formula

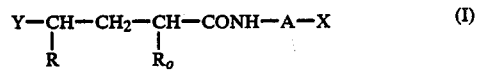

wherein X and Y independently represent hydroxymethyl; cyano; carboxy; functionally modified carboxy selected from esterified carboxy, carbamoyl, and N-substituted carbamoyl; 5-tetrazolyl; 2-oxazolyl, 4,5-dihydro-2-oxazolyl, 2-imidazolyl or 4,5-dihydro-2-imidazolyl or any said grouping substituted by lower alkyl; R and $R_0$ independently represent hydrogen, lower alkyl, ($C_3$–$C_7$)-cycloalkyl-lower alkyl, or aryl-lower alkyl in which aryl represents phenyl, pyridyl, thienyl, furyl, biphenyl or naphthyl, each unsubstituted or mono- or di-substituted by halogen, lower alkyl, hydroxy, acyloxy, lower alkoxy, trifluoromethyl or cyano; A represents straight chain ($C_2$–$C_5$)-alkylene; or A represents straight chain ($C_2$–$C_5$)-alkylene substituted by lower alkyl, by lower alkylthio-lower alkyl, by hydroxy-lower alkyl, by acyloxy-lower alkyl, by lower alkoxy-lower alkyl, by amino or acyl-amino, by aminolower alkyl, by acylamino-lower alkyl, by ($C_3$–$C_7$)-cycloalkyl, by ($C_3$–$C_7$)-cycloalkyl-lower alkyl, by aryl or aryl-lower alkyl in which aryl represents phenyl or phenyl mono- or disubstituted by halogen, lower alkyl, lower alkoxy, hydroxy, acyloxy, trifluoromethyl or cyano; or A represents phenylene or cyclohexylene; pharmaceutically acceptable prodrug derivatives of any said compounds having a free carboxy group; pharmaceutically acceptable salts of any said compounds with a salt-forming group; methods for synthesis; pharmaceutical compositions thereof; and use thereof as enkephalinase inhibitors.

14 Claims, No Drawings

N-SUBSTITUTED BUTYRAMIDE DERIVATIVES USEFUL FOR TREATMENT OF CONDITIONS RESPONSIVE TO INHIBITION OF ENKEPHALINASE

This application is a continuation of application Ser. No. 772,067, filed 9/3/85, which is a continuation-in-part of application Ser. No. 618,617 filed Jun. 8, 1984, now abandoned.

SUMMARY OF THE DISCLOSURE

The present invention concerns and has for its object new butyramide derivatives corresponding to Formula I

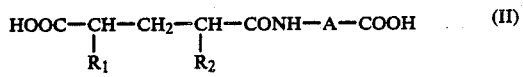

wherein X and Y independently represent hydroxymethyl; cyano; carboxy; functionally modified carboxy selected from esterified carboxy, carbamoyl, and N-substituted carbamoyl; 5-tetrazolyl; 2-oxazolyl, 4,5-dihydro-2-oxazolyl, 2-imidazolyl or 4,5-dihydro-2-imidazolyl or any said grouping substituted by lower alkyl; R and $R_o$ independently represent lower alkyl, $(C_3-C_7)$-cycloalkyl-lower alkyl, or aryl-lower alkyl in which aryl represents phenyl, pyridyl, thienyl, furyl, Diphenyl or naphthyl, each unsubstituted or mono- or di-substituted by halogen, lower alkyl, hydroxy, acyloxy, lower alkoxy, trifluoromethyl or cyano; A represents straight chain $(C_2-C_5)$-alkylene; or A represents straight chain $(C_2-C_5)$-alkylene substituted by lower alkyl, by lower alkylthio-lower alkyl, by hydroxy-lower alkyl, by acyloxy-lower alkyl, by lower alkoxy-lower alkyl, by amino or acyl-amino, by amino-lower alkyl, by acylamino-lower alkyl, by $(C_3-C_7)$-cycloalkyl, by $(C_3-C_7)$-cycloalkyl-lower alkyl, by aryl or aryl-lower alkyl in which aryl represents phenyl or phenyl mono- or disubstituted by halogen, lower alkyl, lower alkoxy, hydroxy, acyloxy, trifluoromethyl or cyano; or A represents phenylene or cylohexylene; or pharmaceutically acceptable prodrug derivatives of any said compounds having a free carboxy group; or pharmaceutically acceptable salts of any said compounds with a salt-forming group; their pharmaceutical compositions; methods for their preparation; and their use as pharmaceutical agents, e.g. as enkephalinase inhibitors in mammals.

The compounds of the invention exhibit valuable pharmacological properties, particularly potentiation of enkephalins by virtue of their ability to inhibit the enkephalin degrading enzyme enkephalinase.

The foregoing attributes render the N-substituted butyramide derivatives of this invention particularly useful when administered, alone or in combination, to mammals e.g. for the treatment of conditions responsive to inhibition of enkephalinase, namely as analgesic, psychotropic (particularly antidepressant and neuroleptic) cardiovascular (particularly antihypertensive), agents.

Compounds of formula I, depending on the nature of R, $R_o$, X, Y and A possess a number of asymmetric carbon atoms. The resulting diastereoisomers and optical antipodes are encompassed by the instant invention.

DESCRIPTION OF THE PREFERRED EMBODIMENTS

More specifically, the instant invention relates to compounds of formula II, namely the glutaric acid derivatives

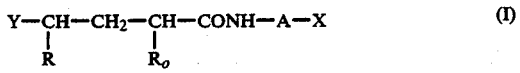

wherein $R_1$ and $R_2$ independently represent lower alkyl, $(C_3-C_7)$-cycloalkyl-lower alkyl, or aryl-lower alkyl in which aryl represents phenyl, pyridyl, thienyl, furyl, biphenyl or napthyl each unsubstituted or mono- or di-substituted by halogen, lower alkyl, hydroxy, lower alkoxy, trifluoromethyl or cyano; A represents straight chain $(C_2-C_5)$-alkylene; or A represents straight chain $(C_2-C_5)$-alkylene substituted by lower alkyl, by lower alkylthio-lower alkyl, by hydroxy-lower alkyl, by acyloxy-lower alkyl, by lower alkoxy-lower alkyl, by amino or acylamino, by amino-lower alkyl, by acylamino-lower alkyl, by $(C_3-C_7)$-cycloalkyl, by $(C_3-C_7)$-cycloalkyl-lower alkyl, by aryl or aryl-lower alkyl in which aryl represents phenyl or phenyl mono- or disubstituted by halogen, lower alkyl, hydroxy, lower alkoxy, trifluoromethyl or cyano; or A represents phenylene or cyclohexylene; a mono- or biscarboxylic acid derivative thereof in which the derivative is selected from an unsubstituted amide or mono- or di-$(C_1-C_{20})$-alkylamide; a tertiary lower alkylene, oxalkylene or azaalkylene amide wherein the lower alkylene, oxalkylene or azaalkylene group together with the amide nitrogen forms a 5-, 6- or 7-membered ring, or said lower alkylene, oxalkylene or azaalkylene amide is substituted on the ring by lower alkyl, hydroxy-(lower)alkyl or by lower alkanoyloxy-(lower) alkyl; an alpha-(lower)-alkoxycarbonyl-or alpha-carboxy-substituted lower alkyl-amide; an alpha(lower)alkoxycarbonyl-or alpha-carboxy-substituted aryl(lower) alkylamide in which aryl represents optionally substituted phenyl or 3-indolyl; an (amino or acylamino)-(lower) alkylamide; a $(C_1-C_{20})$ alkyl ester; an (amino, acylamino, mono- or di-lower alkylamino, carboxy or lower carboalkoxy)-substituted lower alkyl ester; an aryl-(lower) alkyl ester in which aryl represents optionally substituted phenyl or pyridyl; a lower alkanoyloxy-(lower) alkyl ester; a 3-phthalidyl or (lower alkyl, lower alkoxy or halo)-substituted 3-phthalidyl ester; a (hydroxy, lower alkanoyloxy or lower alkoxy)-substituted (lower) alkoxymethyl ester; a bicycloalkyloxycarbonyl-lower alkyl ester having up to 10 carbon atoms in the bicycloalkyl group; a hydroxyamide; a lower alkylsulfonylamide; a 1-(lower alkoxycarbonyloxy)-lower alkyl ester; a 3-cholestanyl or 3-cholestenyl ester; a monosaccharidyl or protected monosaccharidyl ester being an ester incorporating as the alcohol portion a monosaccharide or protected monosaccharide, e.g. a free or protected aldopentose or aldohexose in straight chain or cyclic form, e.g., furanose or pyranose form, or a free or protected glyconic acid of 5 or 6 carbon atoms or a lactone thereof; a polyhydroxy-lower alkyl or protected polyhydroxy-lower alkyl ester being an ester incorporating as the alcohol portion a polyhydroxy-lower alkane or protected polyhydroxy-lower alkane, e.g. a free or protected glycerol or erythritol; and pharmaceutically acceptable salts of any said compound with a salt forming group.

More particularly, the instant invention relates to the compounds of formula III

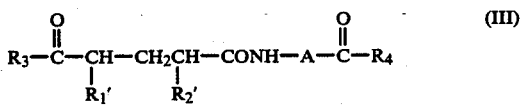

wherein $R_1'$ and $R_2'$ independently represent lower alkyl or aryl-$(C_1–C_4)$-alkyl in which aryl represents phenyl or phenyl mono- or di-substituted by halogen, lower alkyl, hydroxy, lower alkoxy, trifluoromethyl or cyano; A represents straight chain $(C_2–C_5)$-alkylene; or A represents $(C_2–C_5)$- straight chain alkylene monosubstituted by lower alkyl, by phenyl or phenyl-lower alkyl, by (halo, lower alkyl, hydroxy, trifluoromethyl or lower alkoxy)-mono- or disubstituted phenyl or phenyl-lower alkyl, by lower alkylthio-lower alkyl, by hydroxy-lower alkyl, by lower alkoxy-lower alkyl, by amino-lower alkyl or by acylamino- lower alkyl; or A represents phenylene or cyclohexylene; $COR_3$ and $COR_4$ represent carboxy, carboxy esterified in form of a pharmaceutically acceptable ester, carbamoyl and N-substituted carbamoyl in which $R_3$ and $R_4$ independently represent hydroxy; $(C_1–C_{20})$-alkoxy; (amino, acylamino, mono- or di-lower alkylamino)-lower alkoxy; carboxy-lower alkoxy; lower alkoxycarbonyl-lower alkoxy; aryl-lower alkoxy in which aryl represents optionally (halogen, lower alkyl, hydroxy or lower alkoxy)-mono- or di-substituted phenyl or pyridyl; (hydroxy, lower alkanoyloxy or lower alkoxy)-lower alkoxy; (hydroxy, lower alkanoyloxy or lower alkoxy)-lower alkoxymethoxy; bicyclo[2,2,1]-heptyloxycarbonyl-lower alkoxy; cholestan-3-oxy or cholest-5-en-oxy; 3-phthalidoxy or (lower alkyl, lower alkoxy or halo)-substituted 3-phthalidoxy; mono- saccharidyloxy or protected monosaccharidyloxy representing e.g. glucosyloxy, galactosyloxy, mannosyloxy, sorbosyloxy, allosyloxy, ribosyloxy, arabinosyloxy, ribonyloxy, gluconyloxy, or cyclic, e.g. appropriate pyranose, furanose or lactone forms thereof, wherein hydroxy groups are free or one or more, as appropriate, are protected in form of esters, e.g. a lower alkanoyl or a benzoyl ester, in form of ethers, e.g. a lower alkyl or benzyl ether, or, in case two vicinal hydroxy groups are involved, in the form of acetals or ketals, e.g. a lower alkylidene, a benzylidene or a 5-or-6-membered cycloalkylidene derivative; polyhydroxy-lower alkoxy or protected polyhydroxy-lower alkoxy representing, e.g., dihydroxy-propyloxy or trihydroxy- butyloxy wherein hydroxy groups are free or one or more, as appropriate, are protected in form of esters, e.g., a lower alkanoyl or a benzoyl ester, in form of ethers, e.g. a lower alkyl or benzyl ether, or, in case two vicinal hydroxy groups are involved, in the form of acetals or ketals, e.g. a lower alkylidene, a benzylidene or a 5-or-6- membered cycloalkylidene derivative; 1-(lower alkoxycarbonyloxy)-lower alkoxy; amino; mono- or di-$(C_1–C_{20})$-alkyl-amino; morpholino; N-lower alkylpiperazino; pyrrolidino; piperidino; perhydroazepino; (amino or acylamino)-lower alkylamino; alpha-(carboxy or lower alkoxycarbonyl)-lower alkylamino; aryl-lower alkylamino in which aryl is phenyl or 3-indolyl and which can be substituted on the alpha-carbon by carboxy or lower alkoxycarbonyl; hydroxyamino; or lower alkylsulfonylamino; and pharmaceutically acceptable salts of any said compounds with a salt forming group.

Any pharmaceutically acceptable prodrug derivatives, e.g. any pharmaceutically acceptable mono- or di-esters and amides of the di-carboxylic acids of this invention that may be convertible by solvolysis or under physiological conditions to the carboxylic acids e.g. esters and amides cited above, represent a particular object of the invention. Preferred as pharmaceutically acceptable prodrug derivatives are the pharmaceutically acceptable mono- or di-esters of said carboxylic acids as defined herein.

Said esters are preferably, e.g., the straight chain or branched alkyl, the pivaloxymethyl, bornyloxycarbonylmethyl, benzyl, pyridylmethyl, alpha-carboxyethyl, esterified alpha-carboxyethyl, 1-(lower alkoxycarbonyloxy)-lower alkyl, 3-phthalidyl, cholestan-3-yl or cholest-5-en-3-yl esters; the monosaccharidyl or protected monosaccharidyl esters being esters incorporating as the alcohol portion a monosaccharide or protected monosaccharide, e.g. a free or protected aldopentose or aldohexose in straight chain or cyclic form, e.g., furanose or pyranose form, or a free or protected glyconic acid of 5 or 6 carbon atoms or a lactone thereof; the polyhydroxy-lower alkyl or protected polyhydroxy-lower alkyl esters being esters incorporating as the alcohol portion a polyhydroxy-lower alkane or protected polyhydroxy-lower alkane, e.g. a free or protected glycerol or erythritol;

Said amides are preferably e.g. simple primary and secondary amides and amides derived from alpha-amino acids or derivatives thereof, such as the amides derived from alanine, phenylalanine.

Preferred are the compounds of formula III wherein $R_1'$ and $R_2'$ independently represent aryl-$(C_1–C_4)$-alkyl in which aryl represents phenyl or phenyl mono- or di-substituted by halogen, lower alkyl, hydroxy, lower alkoxy, trifluoromethyl or cyano; A represents $(C_2–C_5)$-straight chain alkylene, $(C_2–C_5)$-straight chain alkylene substituted by lower alkyl, phenyl, halophenyl or substituted by phenyl-lower alkyl; or A represents phenylene or cyclohexylene; $R_3$ and $R_4$ independently represent hydroxy; $(C_1–C_{20})$-alkoxy; (amino, mono- or di-lower alkylamino)-lower alkoxy; alpha-carboxy-lower alkoxy; alpha-lower alkoxycarbonyl-lower alkoxy; arylmethoxy in which aryl represents phenyl, pyridyl, or (halogen, lower alkyl or lower alkoxy)-monosubstituted phenyl or pyridyl; (lower alkanoyloxy or lower alkoxy)-methoxy; (hydroxy, lower alkanoyloxy or lower alkoxy)-ethoxymethoxy; bicyclo[2,2,1]heptyloxycarbonylmethoxy; 1-(lower alkoxycarbonyloxy)-lower alkoxy; 3-phthalidoxy or (lower alkyl, lower alkoxy or halogen)-substituted 3-phthalidoxy; cholestan-3-oxy or cholest-5-en-3-oxy; monosaccharidyloxy or protected monosaccharidyloxy selected from glucosyloxy, galactosyloxy, mannosyloxy, sorbosyloxy, allosyloxy, ribosyloxy, arabinosyloxy, ribonyloxy, gluconyloxy, or cyclic, e.g. appropriate pyranose, furanose or lactone forms thereof, wherein hydroxy groups are free or one or more, as appropriate, are protected in form of a lower alkanoyl or a benzoyl ester, in form of a lower alkyl or benzyl ether, or, in case two vicinal hydroxy groups are involved, in the form of a lower alkylidene, a benzylidene or a 5-or-6-membered cycloalkylidene derivative; polyhydroxy-lower alkoxy or protected polyhydroxy-lower alkoxy selected from dihydroxy-propyloxy or trihydroxybutyloxy wherein hydroxy groups are free or one or more, as appropriate, are protected in form of a lower alkanoyl or a benzoyl ester, in form of a lower alkyl or benzyl ether, or, in case two vicinal hydroxy groups are involved, in the form of a lower alkylidene, a benzylidene or a 5-or 6-membered cycloalkylidene derivative; amino; mono- or di-($C_1$-$C_{20}$)-alkylamino; morpholino; N-methylpiperazino; piperidino; perhydroazepino; amino-lower alkylamino; alpha-(carboxy or alpha-lower alkoxycarbonyl)-lower alkylamino; phenylalpha-(carboxy or lower alkoxycarbonyl)- lower alkylamino; hydroxyamino; or lower alkylsulfonyl- amino; and pharmaceutically acceptable salts of any said compounds with a basic or acidic salt forming group.

Further preferred are the above compounds of formula III wherein $R_3$ and $R_4$ independently represent hydroxy; ($C_1$-$C_{20}$)-alkoxy; pivaloyloxymethoxy; bornyloxycarbonylmethoxy; benzyloxy; pyridylmethoxy; alpha-carboxyethoxy; alpha-lower alkoxycarbonylethoxy; 3-phthalidoxy; monosaccharidyloxy or protected monosaccharidyloxy selected from glucofuranosyloxy, glucopyranosyloxy, galactopyranosyloxy, allofuranosyloxy, mannofuranosyloxy, ribofuranosyloxy, sorbofuranosyloxy, arabinofuranosyloxy and ribono(1,4-lactone)-yloxy, wherein hydroxy groups are free or hydroxy groups are protected in form of a lower alkanoyl ester, in form of a benzyl ether or in form of an isopropylidene, a benzylidene or cyclohexylidene derivative; amino, mono- or di-lower alkylamino; morpholino; alpha-(carboxy or lower alkoxycarbonyl)-lower alkylamino; or lower alkylsulfonylamino; and pharmaceutically acceptable salts of any said compounds with a basic or acid salt forming group.

Further preferred are the compounds of formula III wherein $R_1'$, $R_2'$ and A have meaning as defined above; $COR_3$ and $COR_4$ represent carboxy or carboxy esterified in form of a pharmaceutically acceptable ester wherein $R_3$ and $R_4$ independently represent hydroxy, lower alkoxy, benzyloxy, pyridylmethoxy, pivaloyloxymethoxy, 3-phthalidoxy, monosaccharidyloxy or protected monosaccharidyloxy as defined above.

Particularly preferred are the above compounds of formula III wherein one of $R_3$ and $R_4$ represents hydroxy and the other of $R_3$ and $R_4$ represents protected monosaccharidyloxy or 3-phthalidoxy.

A specific embodiment of the invention is represented by the glutaric acid derivatives of formula IV

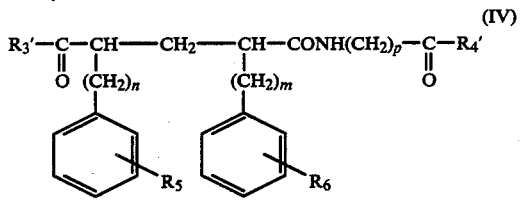

(IV)

wherein m and n independently represent an integer from 1 to 4; p represents an integer from 2 to 4; $R_3'$ and $R_4'$ represent hydroxy; $R_5$ and $R_6$ independently represent hydrogen, halogen, hydroxy, lower alkoxy, lower alkyl or trifluoromethyl; or a pharmaceutically acceptable mono- or di-(ester or amide) pro-drug derivative thereof; and pharmaceutically acceptable salts of any salts of any said compounds with a free carboxy group or basic salt forming group.

A further embodiment of the invention is represented by the compounds of formula IV wherein m and n independently represent an integer from 1 to 4; p represents an integer from 2 to 4; $R_3'$ and $R_4'$ independently represent hydroxy, ($C_1$-$C_{20}$)-alkoxy, amino, pivaloyloxymethoxy, bornyloxycarbonylmethoxy, benzyloxy, pyridylmethoxy, 3-phthalidoxy, 1-(lower alkoxycarbonyloxy)-lower alkoxy; monosaccharidyloxy or protected monosaccharidyloxy selected from glucofuranosyloxy, glucopyranosyloxy, galactopyranosyloxy, allofuranosyloxy, mannofuranosyloxy, ribofuranosyloxy, sorbofuranosyloxy, arabinofuranosyloxy and ribono(1,4-lactone)-yloxy, wherein hydroxy groups are free or hydroxy groups are protected in form of a lower alkanoyl ester, in form of a benzyl ether or in form of an isopropylidene, a benzylidene or cyclohexylidene derivative; or lower alkylsulfonylamino; $R_5$ and $R_6$ independently represent hydrogen, halogen, hydroxy, lower alkoxy, lower alkyl or trifluoromethyl; and pharmaceutically acceptable salts of any said compounds with a free carboxy group or basic salt forming group.

Further preferred are the compounds of formula IV wherein m and n represent the integer 1 or 2; p represents the integer 2 or 3; $R_3'$ and $R_4'$ independently represent hydroxy, lower alkoxy, pivaloyloxymethoxy, pyridylmethoxy, benzyloxy, amino, lower alkylsulfonylamino, 3-phthalidoxy, monosaccharidyloxy or protected saccharidyloxy as defined above; and $R_5$ and $R_6$ have meanings described above.

Most preferred are the compounds of formula IV wherein m and n represent the integer 1; p represents the integer 2 or 3; $R_5$ and $R_6$ represent hydrogen; $R_3'$ and $R_4'$ represent hydroxy; pharmaceutically acceptable ester and amide prodrug derivarives thereof as defined herein; and pharmaceutically acceptable salts thereof.

Preferred as prodrug derivatives of the compounds of formula IV wherein $R_3'$ and $R_4'$ represent hydroxy are the compounds of formula IV wherein either one or both of $R_3'$ and $R_4'$ represent lower alkoxy of 1 to 4 carbon atoms, 3-pyridylmethoxy, benzyloxy, pivaloyloxmethoxy, 3-phthalidoxy, bornyloxycarbonylmethoxy, 1-(ethoxycarbonyloxy)-ethoxy, or amino; and pharmaceutically acceptable salts thereof.

Also preferred as prodrug derivatives of the compounds of formula IV wherein $R_3'$ and $R_4'$ represent hydroxy are the monosaccharidyl esters wherein one of $R_3'$ and $R_4'$ represents preferably 1,2:5,6-di-O-isopropylidene-D-glucofuranos-3-yloxy, 1,2:3,4-di-O-isopropylidene-D-galactopyranos-6-yloxy, 2,3-O-isopropylidene-D-ribono-(1,4-lactone)-5-yloxy, 2,3:5,6-di-O-cyclohexylidene-D-manno-furanos-1-yloxy, 2,3-O-cyclohexylidene-D-ribono-(1,4-lactone)-5-yloxy, 1-methyl-2,3-O-isopropylidene-D-ribofur-anos-5-yloxy, 1,2-O-isopropylidene-D-glucofuranos-3-yloxy, 2,3:4,6-di-O-isopropylidene-L-sorbofuranos-1-yloxy, 1,2:5,6-di-O-isopropylidene-D-allofuranos-3-yloxy, 2,3:5,6-di-O-isopropylidene-D-mannofuranos-1-yloxy, 2,3,5-tri-O-benzyl-D-arabofuranos-1-yloxy, 2,3,4,6-tetra-O-benzyl-D-glucopyranos-1-yloxy or 2,3-O-benzylidene-D-ribono-(1,4-lactone)-5-yloxy, and the other of $R_3'$ and $R_4'$ represents hydroxy, lower alkoxy of 1 to 4 carbon atoms, pyridylmethoxy, benzyloxy or pivaloyloxymethoxy.

Further preferred as prodrug derivatives of the compounds of formula IV wherein $R_3'$ and $R_4'$ represent hydroxy are said compounds of formula IV wherein one of $R_3'$ and $R_4'$ represents 3-phthalidoxy, 1,2:3,4-di-O-isopropylidene-D-galactopyranos-6-yloxy, 1,2:5,6-di-O-isopropylidene-D-glucofuranos-3-yloxy, 2,3-isopropylidene-D-ribono-(1,4-lactone)-5-yloxy or 2,3-O-benzylidene-D-ribono-(1,4-lactone)-5-yloxy, and the other of $R_3'$ and $R_4'$ represents hydroxy; and pharmaceutically acceptable salts thereof.

The compounds of the invention, of formula I–IV and derivatives may contain several asymmetric carbon atoms, depending on the nature of the substituents.

Thus the compounds of the invention exist in the form of stereoisomers, e.g., racemates, pure enantiomers, or mixtures thereof, all of which are within the scope of the invention.

For example, the compounds of formula I (wherein R and/or $R_o$ represent substituents other than hydrogen) exist in isomeric forms, e.g. wherein the asymmetric carbon atoms on the glutanyl chain bearing the R and $R_o$ groups may exist either in the S or R configuration.

The compounds of the invention, e.g. those of formula I having said two asymmetric centers exist as two distinct racemic diastereoisomeric forms which may be called erythro and threo depending on the relative orientation of the R and $R_o$ substituents on the chain. Each of the two racemates consists of the optically active enantiomers (or antipodes) having the (S,S), (R,R) and (R,S), (S,R) configurations, respectively.

Preferred are the threo racemic compounds and particularly the enantiomeric form thereof depicted in formula Ia

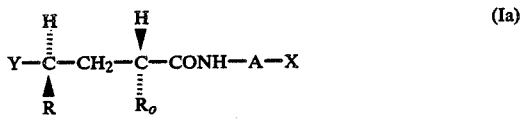

and wherein A, X, Y, R, $R_o$ have meaning as defined herein above for compounds of formula I.

For the glutaric acid derivatives of formula II (and esters and amides thereof) and of formula III and IV wherein both $R_1$ and $R_2$ (or $R_1'$ and $R_2'$) represent substituents other than hydrogen, the glutaryl chain likewise exists in two distinct diastereomeric forms which may be called erythro and threo respectively. Preferred are e.g. the compounds of formula IV as the threo diastereoisomer (racemate), more particularly as the enantiomeric form wherein the glutaryl portion is as depicted in formula IVa

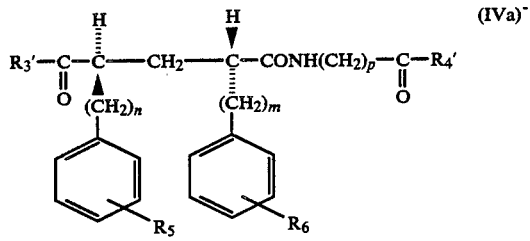

and wherein $R_3'$, $R_4'$, $R_5$, $R_6$, m, n and p have meaning as defined hereinabove for compounds of formula IV.

Illustrative thereof, in the above compounds of formula IVa wherein m and n represent the integer 1, each of the two carbon atoms on the glutaryl chain carrying said substituent is assigned the (S)-configuration; in said compounds of formula IVa wherein m and n represent an integer from 2 to 4, each of the two carbon atoms is assigned the (R)-configuration.

The general definitions used herein unless denoted otherwise have the following meanings within the scope of the present invention.

Aryl represents a carbocyclic or heterocyclic aromatic radical preferably being phenyl, 2- or 3- thienyl, o-, m- or p-biphenyl, 2 or 3-indolyl, 2-, 3-or 4-pyridyl, 1- or 2-naphthyl, 2- or 3-furyl, each optionally substituted by lower alkyl, lower alkoxy, lower alkylenedioxy, hydroxy, lower alkanoyloxy, halogen or trifluoromethyl.

Optionally substituted phenyl represents preferably phenyl or phenyl substituted by one to three of lower alkyl, lower alkoxy, halogen or trifluoromethyl.

Aryl, as in aryl-lower alkyl, is preferably phenyl or phenyl substituted by one to three of lower alkyl, lower alkoxy, hydroxy, halogen or trifluoromethyl; and aryl-lower alkyl is advantageously benzyl or phenethyl optionally substituted by one to three of lower alkyl, lower alkoxy, hydroxy, lower alkanoyloxy, halogen or trifluoromethyl.

$C_1$–$C_{20}$ Alkyl represents branched or unbranched alkyl with 1 to 20 carbon atoms.

Phenylene represents o-, m- or p-phenylene.

Cyclohexylene represents 1,2-, 1,3-, and preferably 1,4-cyclohexylene.

Straight chain $C_2$–$C_5$-alkylene represents preferably ethylene or propylene.

The term cycloalkyl represents a cyclic hydrocarbon radical which preferably contains 3 to 7 ring carbons and is, for example, cyclopentyl or cyclohexyl.

The term cycloalkyl(lower)alkyl represents preferably 1- or 2-(cyclopentyl or cyclohexyl)ethyl, 1-, 2-or 3-(cyclopentyl or cyclohexyl)propyl, or 1-, 2-, 3- or 4-(cyclopentyl or cyclohexyl)-butyl.

The term "lower" referred to above and hereinafter in connection with organic radicals or compounds respectively defines such with up to and including 7, preferably up and including 4 and advantageously one or two carbon atoms.

A lower alkyl group preferably contains 1–4 carbon atoms and represents for example ethyl, propyl, butyl or advantageously methyl.

A lower alkoxy group preferably contains 1–4 carbon atoms and represents for example methoxy, propoxy, isopropoxy or advantageously ethoxy.

A mono-lower alkylamino group preferably contains 1–4 carbon atoms in the alkyl portion and is for example N-methylamino, N-propylamino or advantageously N-ethylamino.

A di-lower alkylamino group preferably contains 1–4 carbon atoms in each lower alkyl portion and represents, for example, N,N-dimethylamino, N-methyl-N-ethylamino and advantageously N,N-diethylamino.

A lower alkoxycarbonyl group preferably contains 1 to 4 carbon atoms in the alkoxy portion and represents, for example, methoxycarbonyl, propoxycarbonyl, isopropoxycarbonyl or advantageously ethoxycarbonyl.

Lower alkylenedioxy represents preferably ethylenedioxy, and advantageously methylenedioxy.

Aryl-lower-alkoxy represents advantageously e.g. benzyloxy, benzyloxy substituted by methyl, methoxy or chloro, and pyridylmethoxy.

Pyridyl represents 2-, 3- or 4-pyridyl.

Carboxy-lower alkoxy represents advantageously e.g. 1-carboxyethoxy.

Lower alkoxycarbonyl-lower alkoxy represents advantageously e.g. 1-(ethoxycarbonyl)ethoxy.

Amino-lower alkoxy, mono-lower alkylamino-lower alkoxy, di-(lower)alkylamino-lower alkoxy advantageously represent respectively e.g. aminoethoxy, ethylaminoethoxy, diethylaminoethoxy.

Hydroxy-lower alkyl is preferably hydroxymethyl, hydroxyethyl or hydroxypropyl, advantageously hydroxymethyl.

Bicycloalkyloxycarbonyl-lower alkoxy preferably represents bicyclo[2,2,1]heptyloxycarbonyl-lower alkoxy unsubstituted or substituted by lower alkyl, advantageously bornyloxycarbonylmethoxy.

Amino-lower alkyl represents preferably amino-(ethyl, propyl or butyl).

Lower alkylidene is preferably isopropylidene.

Cycloalkylidene is preferably cyclohexylidene.

Halogen preferably represents chlorine, but may also be bromine, fluorine or iodine.

Lower alkanoyl is preferably acetyl, propionyl, butyryl, or pivaloyl.

Acyl is acyloxy, acyloxy-lower alkyl, acylamino, acylamino-lower alkyl represents lower alkanoyl, aroyl, lower alkoxycarbonyl, or di-lower alkylcarbamoyl, preferably lower alkanoyl.

Aroyl is preferably benzoyl or benzenesulfonyl; benzoyl or benzenesulfonyl substituted by one to three of lower alkyl, lower alkoxy, halogen or trifluoromethyl; or heteroaroyl, e.g. thienoyl, pyrroloyl, 2-, 3-, or 4-pyridylcarbonyl advantageously nicotinoyl.

Lower alkanoyloxy is preferably acetoxy, pivaloyloxy or propionyloxy; lower alkanoylamino is preferably acetamido or propionamido; aroyloxy is preferably benzene-sulfonyloxy, benzoyloxy, benzoyloxy or benzenesulfonyloxy substituted on the benzene ring by one to three of lower alkyl, lower alkoxy, halogen or trifluoromethyl, or heteroaroyloxy.

Heteroaroyloxy is preferably 2-, 3- or 4-pyridylcarbonyloxy, advantageously nicotinoyloxy.

Acylamino represents lower alkanoylamino, aroylamino, heteroaroylamino, lower alkoxycarbonylamino, or di-lower alkylcarbamoylamino, preferably lower alkanoylamino.

Acylamino-lower alkyl represents preferably acylamino(ethyl, propyl or butyl).

Mono- or di-lower alkylcarbamoyl is preferably mono- or di-N-(methyl, ethyl, propyl)-carbamoyl.

Functionally modified carboxy represents esterified carboxy, carbamoyl or carbamoyl substituted on nitrogen.

Esterified carboxy represents preferably carboxy esterified in form of a pharmaceutically acceptable ester, advantageously an ester that may be convertible by solvolysis or under physiological conditions to the free carboxylic acid, e.g. especially optionally substituted alkoxycarbonyl in which optionally substituted lower alkoxy represents preferably $C_1$–$C_{20}$ alkoxy, advantageously lower alkoxy; (amino, acylamino, mono- or di-lower alkylamino)-lower alkoxy; carboxy- lower alkoxy, e.g. alpha-carboxy-lower alkoxy; lower alkoxycarbonyl-lower alkoxy, e.g. alpha-lower alkoxycarbonyl-lower alkoxy; aryl-lower alkoxy, preferably optionally (halo, lower alkyl or lower alkoxy)benzyloxy or pyridyl-methoxy; (hydroxy, lower alkanoyloxy or lower alkoxy)-lower alkoxy, e.g. pivaloyloxymethoxy; (hydroxy, lower alkanoyloxy or lower alkoxy)-lower alkoxymethoxy; bicycloalkoxycarbonyl-lower alkoxy, e.g. bicyclo[2,2,1]-heptyloxycarbonyl-lower alkoxy, especially bicyclo[2,2,1]-heptyloxycarbonylmethoxy such as bornyloxycarbonylmethoxy; 1-(lower alkoxycarbonyloxy)-lower alkoxy.

Esterified carboxy also represents 3-phthalidoxycarbonyl and (lower alkyl, lower alkoxy, or halo)-substituted 3-phthalidoxycarbonyl.

Esterified carboxy further represents:

(a) cholestan-3-oxycarbonyl or cholest-5-en-3-oxycarbonyl;

(b) monosaccharidyloxycarbonyl or protected monosaccharidyloxy carbonyl in which monosaccharidyloxy and protected monosaccharidyloxy represent preferably glucosyloxy, galactosyloxy, mannosyloxy, sorbosyloxy, allosyloxy, ribosyloxy, arabinosyloxy, ribonyloxy, gluconyloxy, or cyclic, e.g. appropriate pyranose, furanose or lactone forms thereof, wherein hydroxy groups are free or one or more, as appropriate, are protected in form of esters, e.g. a lower alkanoyl or a benzoyl ester, in form of esthers, e.g. a lower alkyl or benzyl ether, or, in case two vicinal hydroxy groups are involved, in the form of acetals or ketals, e.g. a lower alkylidene, a benzylidene or a 5-or-6-membered cycloalkylidene derivative;

(c) polyhydroxy-lower alkoxycarbonyl or protected polyhydroxy-lower alkoxycarbonyl in which polyhydroxy-lower alkoxy and protected polyhydroxy-lower alkoxy represent preferably dihydroxypropyloxy or trihydroxybutyloxy wherein hydroxy groups are free or one or more, as appropriate, are protected in form of esters, e.g., a lower alkanoyl or a benzoyl ester, in form of ethers, e.g. a lower alkyl or benzyl ether, or, in case two vicinal hydroxy groups are involved, in the form of acetals or ketals, e.g. a lower alkylidene, a benzylidene or a 5-or-6-membered cycloalkylidene derivative.

Protected monosaccharidyloxy represents preferably 1,2:5,6-di-O-isopropylidene-D-glucofuranos-3-yloxy, 1,2:3,4-di-O-isopropylidene-D-galactopyranos-6-yloxy, 2,3-O-isopropylidene-D-ribono-(1,4-lactone)-5-yloxy, 2,3:5,6-di-O-cyclohexylidene-D-manno-furanos-1-yloxy, 2,3-O-cyclohexylidene-D-ribono-(1,4-lactone)-5-yloxy, 1-methyl-2,3-O-isopropylidene-D-ribofuranos-5-yloxy, 1,2-O-isopropylidene-D-glucofuranos-3-yloxy, 2,3:4,6-di-O-isopropylidene-L-sorbofuranos-1-yloxy, 1,2:5,6-di-O-isopropylidene-D-allofuranos-3-yloxy, 2,3:5,6-di-O-isopropylidene-D-mannofuranos-1-yloxy, 2,3,5-tri-O-benzyl-D-arabofuranos-1-yloxy, 2,3,4,6-tetra-O-benzyl-D-glucopyranos-1-yloxy or 2,3-O-benzylidene-D-ribono-(1,4-lactone)-5-yloxy.

Protected polyhydroxy-lower alkoxy represents preferably (2,2-dimethyl-1,3-dioxolan-4-yl)-methoxy.

Optionally substituted carbamoyl represents optionally substituted aminocarbonyl in which optionally substituted amino represents preferably amino; lower alkylamino; di-lower alkylamino; morpholino; N-lower alkyl piperazino; pyrrolidino; piperidino; perhydroazepino; (amino or acylamino)-lower alkylamino; alpha-(carboxy or lower alkoxycarbonyl)-lower alkylamino; aryl-lower alkylamino in which aryl is preferably phenyl or indolyl and which can be substituted on the alpha-carbon by carboxy or lower alkoxycarbonyl; hydroxyamino; or lower alkyl sulfonylamino.

Pharmaceutically acceptable salts are acid addition salts, which are preferably such of therapeutically acceptable inorganic or organic acids, such as strong mineral acids, for example hydrohalic, e.g. hydrochloric or hydrobromic acid, sulfuric, phosphoric or nitric acid; aliphatic or aromatic carboxylic or sulfonic acids, e.g. formic, acetic, propionic, succinic, glycollic, lactic, malic, tartaric, gluconic, citric, maleic, fumaric, pyruvic, phenylacetic, benzoic, 4-aminobenzoic, anthranilic, 4-hydroxybenzoic, salicylic, 4-aminosalicyclic, pamoic, nicotinic, methanesulfonic, ethanesulfonic, hydroxyethanesulfonic, benzenesulfonic, p-toluenesulfonic, naphthalenesulfonic, sulfanilic, cyclohexylsulfamic acid; or ascorbic acid.

The novel compounds of the invention are pharmacologically potent enkephalinase inhibitors. The compounds thus increase the level of endogenous enkephalins, e.g. met-enkephalin and leu-enkephalin, in mammals via inhibition of their degradation by the enzyme enkephalinase.

The enkephalin modulating properties render the compounds of the invention useful e.g. as analgesic, neuroleptic or antihypertensive agents.

The above cited properties are demonstrable in vitro and in vivo tests, using advantageously mammals, e.g. mice, rats, dogs, monkeys or isolated organs, tissues and preparations thereof. Said compounds can be applied in vitro in the form of solutions, e.g. preferably aqueous solutions, and in vivo either enterally, parenterally, advantageously intravenously, or intracerebroventricularly, e.g. as a suspension or in aqueous solution. The dosage in vitro may range between about $10^{-4}$ molar and $10^{-9}$ molar concentrations. The dosage in vivo may range depending on the route of administration, between about 0.001 and 50 mg/kg, preferably between about 0.005 and 30 mg/kg, advantageously between about 0.01 and 20 mg/kg.

The analgesic activity is demonstrable by potentiation of the analgesic effects of enkephalin and derivatives thereof, and by classical analgesic tests, such as the phenyl-p-benzoquinone induced writing test [J. Pharmacol. Exp. Therap. 125, 237 (1959)] and the hot plate test in the mouse [J. Pharmaol. Exp. Therap. 107, 385 (1953)].

The antihypertensive activity may be determined in the spontaneously hypertensive rat, Goldblatt rat or dog by direct measurement of systolic blood pressure.

The enkephalinane inhibitory activity is determined in vitro by an adaptation of the method of Alstein et al. as described in Life Sciences 28, 185 (1981), as follows:

A mixture of a solution of the test compound in distilled water or distilled water and ethanol diluted with pH 6-5 buffer and of a synaptic membrane preparation from rat striatum is incubated at pH 6-5 with $^3$H-Leu-enkephalin for 15 minutes at 30° C., in the presence of $10^{-6}$M Bestatin (to inhibit aminopeptidase activity). The reaction is stopped by the addition of 30% acetic acid and the reaction product $^3$H-Tyr-gly-gly is separated from unreacted $^3$H-Leu-enkephalin on a Porapak O column followed by a $Cu^{++}$-chelex column. The $^3$H-Tyr-gly-gly is counted by liquid scintillation. The amount of $^3$H-Tyr-gly-gly generated in the presence of test compound as compared to control is then calculated. An $IC_{50}$ value representing the concentration of test compound required for 50% inhibition of $^3$H-Tyr-gly-gly generation is then determined graphically.

The enkephalinase inhibitory activity can be determined in vivo, e.g. by measuring the potentiation of the analgesic activity of intracerebrally administered D-Ala$^2$-met$^5$-enkephalinamide or met-enkephalin in mice. The enkephalinase inhibitory activity is also determined in vivo by measuring the increase in endogenous brain enkephalin levels, or by direct measurement of striatum enkephalinase activity in mice.

The analgesic activity can be measured by the hot-plate test method in the mouse as follows and essentially as described in J. Pharmacol. Exp. Therap. 107, 385 (1953).

The compound is administered intravenously or intracerebroventricularly 15 minutes prior to the measurement of the response latency. Male CF, (Charles River) mice (20 g) are allowed food and water ad libitum up to the time of testing. The hot plate test for analgesia utilizes an apparatus with an electrically heated, thermostatically controlled copper plate (Analgesia Meter). A Plexiglas cylinder, 2.5 cm×16 cm (inner diameter) and open at both ends, confines the mice to the central area of the hot plate. The surface temperature is maintained at 55°±0.5° C. Response latency is recorded as the time (seconds) from contact with the hot plate until a jump occurs or at 240 seconds if no response occurs within this time. Animals are individually tested at 15 minutes following intravenous or intracerebroventricular (ICV) injection. Intracerebroventricular injections into the lateral ventricle are carried out according to the method of Haley and McCormick, as described in Brit. J. Pharmacol. 12; 12, 1957.

The mean response latency and standard error are calculated. Significance is determined using Student's unpaired t-test, 2-tailed comparison. The test agent is considered to have analgesic activity if the mean response latency is significantly higher than that of the vehicle-treated control group.

The dose of test compound which significantly increases the mean response latency represents an effective analgesic dose.

Illustrative of the invention, N-[(R*,R*)-2,4-dibenzyl-4-carboxybutyryl]-4-aminobutyric acid and N-[(R*,R*)-2,4-dibenzyl-4-carboxybutyryl]-3-aminopropionic acid having an $IC_{50}$ for inhibition of enkephalinase of about $2\times10^{-8}$M for each. N-(2S,4S-dibenzyl-4-carboxybutyryl)-3-aminopropionic acid has an $IC_{50}$ of about $8\times10^{-9}$M.

Further illustrative of the invention, N-[(R*,R*)-2,4-dibenzyl-4-carboxybutyryl]-4-aminobutyric acid and N-[(R*,R*)-2,4-dibenzyl-4-ethoxycarbonylbutyryl]-3-aminopropionic acid increase the mean response latency in mice in the hot plate test procedure for analgesia at dose of about 0.1 μg and 0.03 μg, respectively, on intracerebroventricular administration.

Similarly, the compound of example 17/10, i.e. 1,2:5,6-di-O-isopropylidene-D-glucofuranos-3-yl N-(2S,4S-dibenzyl-4-carboxybutyryl)-3-aminopropionate is effective in the hot plate test at a dose of 30 mg/kg i.v. and lower.

Also illustrative of the invention, N-[(R*,R*)-4-ethoxycarbonyl-2,4-dibenzylbutyryl]-3-aminpropionic acid potentiates the analgesic effect of met-enkephalin (20 μg) at a dose of about 0.01 μg on intracerebroventricular administration.

Similarly, the compound of example 17/6, i.e. 2,3-O-isopropylidene-D-ribono-(1,4-lactone)-5-yl N-(2S,4S-dibenzyl-4-carboxybutyryl)-3-aminopropionate potentiates the analgesic effect of D-Ala$^2$-Met$^5$-enkephalinamide at a dose of 30 mg/kg s.c.

Accordingly the compounds are valuable pharmacological agents, particularly as enkephalinase inhibitors in mammals, especially for relieving pain, psychotic conditions and hypertension in mammals. The compounds of the invention are also useful in the preparation of corresponding pharmaceutical compositions.

The compounds of the invention of formula I are prepared using conventional chemical methodology as applied to e.g. the following process which comprises: condensing a compound of formula V $NH_2$-A-X  (V)

wherein A and X have meaning as defined above, namely wherein A represents straight chain $(C_2–C_5)$-alkylene; or A represents straight chain $(C_2–C_5)$-alkylene substituted by lower alkyl, or lower alkylthio-lower alkyl, by hydroxy-lower alkyl, by acyloxy-lower alkyl, by lower alkoxy-lower alkyl, by amino or acylamino, by amino-lower alkyl, by acylamino-lower alkyl, by $(C_3–C_7)$-cycloalkyl, by $(C_3–C_7)$-cycloalkyl-lower alkyl, by aryl or aryl-lower alkyl in which aryl represents phenyl or phenyl mono- or disubstituted by halogen, lower alkyl, lower alkoxy, hydroxy, acyloxy, trifluoromethyl or cyano; or A represents phenylene or cyclohexylene; and X represents hydroxymethyl, cyano, carboxy; functionally modified carboxy selected from esterified carboxy, carbamoyl and N-substituted carbamoyl; 5-tetrazolyl; 2-oxazolyl, 4,5-dihydro-2-oxazolyl, 2-imidazolyl or 4,5-dihydro-2-imidazolyl or any said grouping substituted by lower alkyl; in temporarily protected form if required; with a compound of formula VI

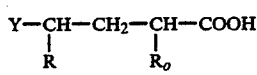

(VI)

or a reactive functional derivative thereof, wherein R, $R_0$ and Y have meaning as defined above, namely wherein R and $R_0$ independently represent lower alkyl, $(C_3–C_7)$-cycloalkyl-lower alkyl, or aryl-lower alkyl in which aryl represents phenyl, pyridyl, thienyl, furyl, biphenyl or naphthyl, each optionally mono- or di-substituted by halogen, lower alkyl, hydroxy, acyloxy, lower alkoxy, trifluoromethyl or cyano; Y represents hydroxymethyl; cyano; carboxy; functionally modified carboxy selected from esterified carboxy, carbamoyl and N-substituted carbamoyl; 5-tetrazolyl; 2-oxazolyl, 4,5-dihydro-2-oxazolyl, 2-imidazolyl or 4,5-dihydro-2-imidazolyl or any said grouping substituted by lower alkyl; in temporarily protected form if required; and, if temporarily protecting any interfering reactive group(s), removing said protecting group(s), and then isolating the resulting compound of the invention; and, if desired, converting a resulting compound of the invention into another compound of the invention, and/or, if desired, converting a resulting free compound into a salt or a resulting salt into the free compound or into another salt, and/or, if desired, separating mixture of isomers or racemates obtained into the single isomers or racemates, and/or, if desired, resolving a racemate obtained into the optical antipodes.

In starting compounds and intermediates therefor which are converted to the compounds of the invention in a manner described herein, functional groups present, such as carboxy, amino and hydroxy groups, are optionally protected by conventional protecting groups that are common in preparative organic chemistry. Protected carboxy, amino and hydroxy groups are those that can be converted under mild conditions into free carboxy, amino and hydroxy groups without other undesired side reactions taking place.

The purpose of introducing protecting groups is to protect the functional groups from undesired reactions with reaction components and under the conditions used for carrying out a desired chemical transformation. The need and choice of protecting groups for a particular reaction is known to those skilled in the art and depends on the nature of the functional group to be protected (carboxy group, amino group etc.), the structure and stability of the molecule of which the substituent is a part, and the reaction conditions.

Well-known protecting groups that meet these conditions and their introduction and removal are described, for example, in J. F. W. McOmie, "Protective Groups in Organic Chemistry", Plenum Press, London, New York 1973, T. W. Greene, "Protective Groups in Organic Synthesis", Wiley, New York 1981, and also in "The Peptides", Vol. I, Schroeder and Luebke, Academic Press, London, New York 1965.

The condensation of an amine of formula V with the acid of formula VI, or a functional reactive derivative thereof, is carried out by methodology well-known in the art.

Reactive functional derivatives of compounds of formula VI are preferably halides, mixed anhydrides such as the pivaloyl, alkoxycarbonyl or cyanoacetyl anhydride, cyclic glutaric anhydrides for compounds of formula VI where Y represents carboxy or the corresponding lactones for compounds of formula VI in which Y represents hydroxymethyl.

The condensation of a compound of formula V in suitably protected form depending on nature of substituents, with a compound of formula VI in the form of a free carboxylic acid is carried out advantageously in the presence of a condensing agent such as dicyclohexylcarbodi- imide or 1,1'-diimidazolylcarbonyl in an inert solvent such as methylene chloride, preferably at room temperature or at a temperature near the boiling point of the solvent.

The condensation of a compound of formula V with the anhydride, as a reactive functional derivative of a compound of formula VI wherein Y represent carboxy, is carried out in an inert solvent such as toluene or methylene chloride, advantageously in the presence of a base, e.g. an inorganic base such as potassium carbonate or an organic base such as triethylamine or pyridine, at a temperature ranging from about 0° to 100°, preferably at room temperature.

The condensation of a compound of formula V with a reactive functional derivative of an acid of formula VI in the form of an acid halide, advantageously an acid chloride, or mixed anhydride, is carried out in an inert solvent under conditions analogous to those described above for condensation with a glutaric acid anhydride, advantageously in the presence of a basic solvent, e.g. pyridine.

The starting materials of Formulae V and VI are known, or, if new, may be prepared according to conventional methods, e.g., those illustrated by the examples herein.

For example, starting materials of formula VI, e.g. wherein Y represents carboxy or functionally modified carboxy, are prepared from the correspondingly substituted glutaric anhydride by hydrolysis, alcoholysis or aminolysis by methods well known in the art for opening of a cyclic anhydride. Monofunctional derivatives of a dicarboxylic acid of formula VI (wherein Y does not represent free carboxy) are converted to the corresponding reactive functional derivative, e.g. an acyl halide, by treatment with e.g. oxalyl chloride in methylene chloride.

The starting substituted glutaric anhydride is prepared by cyclization of the correspondingly substituted glutaric acid by treatment with e.g. acetyl chloride.

The substituted glutaric acids are prepared by methods well-known in the art, e.g. by condensation of the appropriately substituted di-lower alkyl malonate with an optionally alpha-substituted acrylic acid derivative or precursor thereof, e.g. as illustrated in Acta Chem. Scand. 1958, 314 for the preparation of dibenzylglutaric acid.

In the case of 2,4-disubstituted glutaric acids, both threo and erythro diastereoisomers are obtained and may be isolated. When both the 2- and 4-substituents are identical, the isomers consist of the racemic (d,1) threo and meso erythro isomers. The racemic (d,1) diastereoisomer can be further resolved into the individual enantiomers by methods well-known in the art.

The compounds of the invention so obtained, can be converted into each other according to conventional methods. Thus, for example, resulting amides or esters may be hydrolyzed with aqueous alkalies, such as alkali metal carbonates or hydroxides. Resulting free acids may be esterified with e.g. said unsubstituted or substituted alkanols or reactive esterified derivatives thereof such as alkyl halides, or diazoalkanes, or free acids are also converted into said metal, ammonium or acid addition salts in conventional manner.

Thus, any resulting free acid or base can be converted into a corresponding metal, ammonium or acid addition salt respectively, by reacting it with an equivalent amount of the corresponding base, basic salt, acid or ion exchange preparation, e.g. said acids with alkali or ammonium hydroxides or carbonates, or e.g. aminoalkyl esters with said inorganic or organic acids respectively. Any resulting salt may also be converted into the free compound, by liberating the latter with stronger acids or bases, respectively. In view of the close relationship between the free compounds and the salts thereof, whenever a compound of the invention, or intermediate, is referred to in this context, a corresponding salt is also intended, provided such is possible or appropriate under the circumstances.

The compounds, including their salts, may also be obtained in the form of their hydrates, or include other solvents used for the crystallization.

Furthermore, the mono or bis functional derivatives of, e.g., the dicarboxylic acids of formula II, wherein either or both carboxy groups are esterified by identical or different radicals, may be prepared by condensing a said diacid, e.g. of formula II or a mono ester derivative thereof, with an esterifying agent of the formula VII $$R_7-Z \quad (VII)$$

wherein Z represents hydroxy or a reactive esterified hydroxyl group; and $R_7$ represents any of the ester radicals defined hereinabove and comprising such as alkyl, e.g. methyl, ethyl, n- or i-propyl or butyl; substituted lower alkyl e.g. ω-amino, ω-(N-methyl or N,N-dimethylamino), alpha-carboxy or -ethoxycarbonyl-(ethyl, propyl or butyl); aryl(lower)alkyl, e.g. benzyl, (methyl-, methoxy-, chloro-)substituted benzyl, or pyridylmethyl; lower alkanoyloxy-lower alkyl, e.g. pivaloyloxymethyl; 3-phthalidyl or (methyl-, methoxy-, chloro-)substituted 3-phthalidyl, (hydroxy-lower alkanoyloxy-, lower alkoxy-)substituted lower alkoxymethyl e.g. β-(hydroxy-, acetyloxy-, methoxy-) ethoxymethyl; bicycloalkyl-oxycarbonyl-(lower) alkyl, e.g. unsubstituted or lower alkyl substituted bicyclo[2,2,1]heptyloxycarbonyl-(lower)alkyl, advantageously bornyloxycarbonylmethyl; 1-(lower alkoxycarbonyloxy)-loweralkyl, e.g. 1-(methoxy-, ethoxy- or propoxy-carbonyloxy)-methyl, ethyl or propyl; protected monosaccharidyl as defined above; or protected polyhydroxyalkyl as defined above.

A reactive esterified hydroxyl group Z in a compound of the formula VII is a hydroxyl group esterified by a strong inorganic or organic acid. Corresponding Z groups are in particular halogen, for example chlorine, bromine or preferably iodine, also sulfonyloxy groups, such as lower alkyl- or arylsulfonyloxy groups, for example methane-, ethane-, benzene- or toluene-sulfonyloxy groups.

The esterification of the carboxyl groups, optionally in salt form, with a compound of formula VII wherein Z represents a reactive esterified hydroxyl group, is performed in a manner known per se, in the presence of for example an organic base, such as an organic amine, for example a tertiary amine, such as tri-lower alkylamine, for example trimethylamine, triethylamine or ethyl-di-isopro- pylamine, an N,N-di-lower-alkyl-aniline, for example N,N-di-methylaniline, a cyclic tertiary amine, such as an N-lower-alkylated morpholine, for example N-methyl-morpholine, a base of the pyridine type, for example pyridine, an inorganic base, for example hydroxides, carbonates, or hydrogen barbonates of alkali metals or alkaline-earth metals, for example sodium, potassium or calcium hydroxide, carbonate or hydrogen carbonate, or a quaternary ammonium base, such as a tetraalkylammonium hydroxide, carbonate or hydrogen carbonate, for example in which alkyl is e.g. methyl, ethyl, propyl, isopropyl, butyl, or the like, or an oxirane, for example a lower 1,2-alkylene oxide, such as ethylene oxide or propylene oxide.

The di-carboxylic acid, e.g. of the formula II, or a monoester thereof is preferably first converted into a salt of one of the stated organic or inorganic bases, especially into the sodium or potassium salt, and is then reacted with a compound of the formula VII. The compounds of formula VII are known or can be prepared by methods well-known to the art.

A compound of the formula VII wherein Z is a reactive esterified hydroxyl group can be prepared in situ. For example, a compound of the formula VII wherein Z is chloro can be converted by treatment with sodium iodide in a solvent, for example in acetone or acetonitrile, into a compound of the formula VII wherein Z is iodo; or esterification can be carried out with a chloro compound of the formula VII in the presence of sodium iodide.

The esterification reaction of carboxylic acids of the invention is performed in a suitable inert solvent or solvent mixture, for example in dimethylformamide, a halogenated hydrocarbon e.g. methylene chloride, carbon tetrachloride or chlorobenzene, a ketone, e.g. acetone, an ester, e.g. ethyl acetate, or a nitrile, e.g. acetonitrile, or mixtures thereof, preferably at room temperature, or if necessary at a reduced or elevated temperature, advantageously at −10° to +40° C., and/or in an inert-gas atmosphere, for example in a nitrogen atmosphere.

Esterification of a carboxylic acid with an alcohol of formula VII wherein Z represents hydroxy is carried out in a manner known per se, preferably in the presence of an acid catalyst e.g. sulfuric acid or boron trifluoride etherate preferably at an elevated temperature, advantageously ranging from about 40° C. to 100° C.

The compounds of the invention wherein R and/or $R_0$, or $R_1$ and/or $R_2$ or $R_1'$ and/or $R_2'$ contain a phenyl ring, or the compounds of the invention wherein A represents phenylene, may be converted to the corresponding compounds of the invention containing a cyclohexyl or cyclohexylene ring, respectively. Such conversion is carried out e.g. by catalytic hydrogenation in the presence of a catalyst such as rhodium, nickel or platinum in a polar medium using procedures well-known in the art and as illustrated in the examples.

In case mixtures of geometrical or optical isomers of the above compounds of Formulae I to VI are obtained, these can be separated into the single isomers by methods in themselves known, e.g., by fractional distillation, crystallization and/or chromatography. Racemic products can likewise be resolved into the optical antipodes, for example, by separation of diastereomeric salts thereof, e.g., for basic compounds by the fractional crystallization of d- or l-(tartrate, mandelate or camphorsulfonate) salts, or for acidic compounds by fractional crystallization of d- or l-(alpha-methylbenzylamine, cinchonidine, cinchonine, quinine, quinidine, ephedrine, dehydroabietylamine, brucine or strychnine)-salts.

The above-mentioned reactions are carried out according to standard methods, in the presence or absence of diluents, preferably such as are inert to the reagents and are solvents thereof, of catalysts, alkaline or acidic condensing or said other agents respectively and/or inert atmospheres, at low temperatures, room temperature or elevated temperatures, preferably near the boiling point of the solvents used, at atmospheric or superatmospheric pressure.

The invention further includes any variant of said processes, in which an intermediate product obtainable at any stage of the process is used as a starting material and any remaining steps are carried out, or the process is discontinued at any stage threof, or in which the starting materials are formed under the reaction conditions, or in which the reaction components are used in the form of their salts or optically pure antipodes. Mainly those starting materials should be used in said reactions, that lead to the formation of those compounds indicated above as being preferred. For example, the compounds of formula IVa or the corresponding threo racemate, are those derived from the corresponding trans-2,4-disubstituted glutaric anhydride.

The present invention additionally relates to the use in mammals of the compounds of the invention and their pharmaceutically acceptable, non-toxic acid addition salts, or pharmaceutical compositions thereof, as medicaments, especially as enkephalinase inhibitors e.g. for the treatment of pain, and of central nervous system and cardiovascular disorders responsive to enkephalinase inhibition.

The present invention also relates to the use of the compounds of the invention for the preparation of pharmaceutical compositions especially pharmaceutical compositions having enkephalinase inhibiting activity.

The pharmaceutical compositions according to the invention are those suitable for enteral, such as oral or rectal, transdermal and parenteral administration to mammals, including man, for the treatment of disorders responsive to e.g. enkephalinase inhibition, such as pain, psychotic disorders or hypertension, comprising an effective amount of a pharmacologically active compound of the invention or pharmaceutically acceptable salts thereof, alone or in combination with one or more pharmaceutically acceptable carriers.

The pharmacologically active compounds of the invention are useful in the manufacture of pharmaceutical compositions comprising an effective amount thereof in conjunction or admixture with excipients or carriers suitable for either enteral or parenteral application. Preferred are tablets and gelatin capsules comprising the active ingredient together with (a) diluents, e.g. lactose, dextrose, sucrose, mannitol, sorbitol, cellulose and/or glycine; (b) lubricants, e.g. silica, talcum, stearic acid, its magnesium or calcium salts and/or polyethyleneglycol; for tablets also (c) binders, e.g. magnesium aluminum silicate, starch paste, gelatin, tragacanth, methylcellulose, sodium carboxymethylcellulose and/or polyvinylpyrrolidone; if desired, (d) disintegrants, e.g. starches, agar, alginic acid or its sodium salt, or effervescent mixtures; and/or (e) absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, the compositions may also contain other therapeutically valuable substances. Said compositions are prepared according to conventional mixing, granulating or coating methods, respectively, and contain about 0.1 to 75%, preferably about 1 to 50%, of the active ingredient.

Suitable formulations for transdermal application include an effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound, optionally with carriers, optionally a rate controlling barrier to deliver the compound to the skin of the host at a controlled and predetermined rate over a prolonged period of time, and means to secure the device to the skin.

A unit dosage for a mammal of about 50 to 70 kg may contain between about 10 and 100 mg of the active ingredient. The dosage of active compound is dependent on the species of warm-blooded animal (mammal), the body weight, age and individual condition, and on the form of administration.

The following examples are intended to illustrate the invention and are not to be construed as being limitations thereon. Temperatures are given in degrees Centigrade. If not mentioned otherwise, all evaporations are performed under reduced pressure, preferably between about 15 and 100 mm Hg.

The prefixes R* and S* as used herein, e.g. when referring to a 2,4-disubstituted-4-carboxybutyryl grouping (a 2,4-disubstituted glutaryl grouping) or derivatized form thereof, are used to indicate the relative configuration of the two asymmetric centres in the racemic form. The prefixes R and S are used to indicate the absolute configuration at each asymmetric center in the enantiomeric form.

EXAMPLE 1

(a) The solution of 0.21 g of 4-aminobutyric acid and 0.50 g of trans-2,4-dibenzylglutaric anhydride in 5 ml of pyridine and 5 ml of methylene chloride is stirred at room temperature overnight. The mixture is concentrated, the residue dissolved in ethyl acetate and the solution is washed with 1N hydrochloric acid, saturated sodium chloride, dried over magnesium sulfate, concentrated, and the residue is recrystallized from ether to yield the N-[(R*,R*)-2,4-dibenzyl-4-carboxybutyryl]-4-aminobutyric acid, melting at 127°–129°; NMR (Me$_2$SO-d$_6$) δ 12.2 (2H, CO$_2$H), 7.82 (t, 1H, J=6 Hz, NH), 7.26 and 7.28 (s, 10H, Ar-H), 3.0 (t, 2H, J=7 Hz, N—CH$_2$), 2.6 (m, 6H), 2.1 (t, 2H, J=8 Hz, —CH$_2$CO$_2$H), 1.6 (m, 4H).

(b) Similarly prepared from meso-2,4-dibenzylglutaric anhydride is N-[(R*,S*)-2,4-dibenzyl-4-carboxybutyryl)]-4-aminobutyric acid melting at 124°–126°; NMR (CDCl$_3$) δ 11.7 (2H, CO$_2$H), 7.3 (s, 11H, Ar-H, NH), 3.1 (m, 2H, NCH$_2$), 2.7 (m, 6H), 2.1 (m, 2H).

(c) Similarly prepared from 2S,4S-dibenzylgluaric anhydride is N-(2S,4S-dibenzyl-4-carboxybutyryl)-4-aminobutyric acid; disodium salt monohydrate, m.p. 108°–113° dec., [α]D= +11.7° (C=1.0 in methanol).

The starting materials are prepared as follows:

6.9 g of 2,4-Dibenzylglutaric acid (*Acta Chem. Scand.* 1958, 12, 314) is refluxed in 50 ml of acetyl chloride for 3 hours, concentrated, diluted with 25 ml of toluene and evaporated to give a mixture of meso (cis)- and racemic (trans)-2,4-dibenzylglutaric anhydride. The residue is dissolved in 8.5 ml of toluene and 1.5 ml of triethylamine and heated to 50° until all the solid dissolves. The solution is left to stand overnight. The solid is collected to yield the trans-2,4-dibenzylglutaric anhydride melting at 153°–155°. Heating under reflux with dioxanewater (1:1) overnight yields racemic (R* , R*)-dibenzylglutaric acid melting at 150°–152°.

The racemic trans-2,4-dibenzylglutaric anhydride can also be isolated directly from the mixture of meso cis- and racemic trans-2,4-dibenzylglutaric anhydride by fractional crystallization with toluene. The mother liquors are then concentrated and upon standing crystallization occurs. After stirring with cyclohexane the solid is collected to yield the (cis)-meso-2,4-dibenzylglutaric anhydride melting at 55°–57°.

The 2S,4S-dibenzylglutaric anhydride [mp 172°–174°; [α]D= −19.1° (c=1 in CHCl$_3$)] is prepared similarly by refluxing 2S,4S-dibenzylglutaric acid in acetyl chloride for 3 hours, concentrating the mixture and recrystallizing from toluene.

The chiral 2S,4S-dibenzylglutaric acid is prepared as follows: To 5.0 g of (R*,R*)-dibenzylglutaric acid in 20 ml of isopropanol is added 0.81 g of triethylamine and the mixture is stirred for 20 minutes. To this mixture is added 0.97 g of d(+)-α-methylbenzylamine in 20 ml of isopropanol and the solution is stirred overnight. The solid is collected and recrystallized twice from isopropanol to yield 2S,4S-dibenzylglutaric acid as the d(+)-α-methylbenzylamine salt melting at 201°–203°; [α]D= −20.4° (c=1 in methanol). To a warm solution of the above salt in 70 ml of water and 30 ml of ethanol is added 1 ml of concentrated hydrochloric acid. After standing 24 hours the solid is collected, washed with water and dried to yield 2S,4S-dibenzylglutaric acid melting at 150°–152°; [α]D= +8.9° (c=2.0 in methanol).

EXAMPLE 2

According to the methods illustrated by the previous example the following compounds are prepared:

(a) N-[(R*,R* -2,4-dibenzyl-4-carboxybutyryl]-3-aminopropionic acid, melting at 122°–124°. N-[(R*,R*)-2,4-dibenzyl-4-carboxybutyryl]-3-aminopropionic acid is converted to the disodium salt by the following procedure: To the solution of 0.38 g of the diacid in 25 ml of methanol:water (2:1) is added 2.0 ml of 1.00N sodium hydroxide. The solution is concentrated to give a solid. Ethanol is added and the suspension is concentrated and the solid is dried at 50° under high vacuum to yield the N-[(R*,R*)-2,4-dibenzyl-4-carboxybutyryl]-3-aminopropionic acid disodium salt.

(b) N-(2S,4S-dibenzyl-4-carboxybutyryl)-3-aminopropionic acid, melting at 142°–144°, [α]D= +25.6° (c=2.0 in methanol);

(c) N-[(R*,S*)-2,4-dibenzyl-4-carboxybutyryl]-3-aminopropionic acid isolated as the disodium salt melting at 250° (dec); NMR (DMSO-d$_6$) δ 8.1 (m, 1H, NH), 7.25 and 7.18 (S, 10H, Ar-H).

(d) N-[(R*,R*)-2,4-dibenzyl-4-carboxybutyryl]-2-aminobenzoic acid melting at 175°–177°; NMR (CDCl$_3$) δ 11.9 (s, 2H, CO$_2$H), 10.74 (s, 1H, NH), 8.84 (d, 1H, J=9 Hz), 8.18 (d, 1H, J=9 Hz), 7.64 (t, 1H, J=9 Hz), 7.27 and 7.20 (s, 11H), 2.9 (m, 6H), 2.0 (m, 2H).

(e) N-[(R*,R*)-2,4-dibenzyl-4-carboxybutyryl]-3-aminobenzoic acid; NMR (CDCl$_3$) δ 11.4 (s, 2H), 7.75 (m, 5H), 7.22 (s, 10H), 2.8 (m, 6H), 2.0 (m, 2H).

(f) N-[(R*,R*)-2,4-dibenzyl-4-carboxybutyryl]-3-aminopropionitrile melting at 123°–125°, from trans-2,4-dibenzylglutaric anhydride and 3-aminopropionitrile.

(g) N-[(R*,R*)-2,4-dibenzyl-4-carboxybutyryl]-4-aminobenzoic acid melting at 234°–236°; NMR (CDCl$_3$) δ 12.3 (2H, CO$_2$H), 10.3 (s, 1H, NH), 7.95 (d, 2H, J=10 Hz), 7.74 (d, 2H, J=10 Hz), 7.3 (s, 10H), 2.72 (m, 6H), 1.8 (m, 2H); disodium salt has melting point >300°.

EXAMPLE 3

According to procedures illustrated by the previous examples are prepared:

(a) N-[(R*,S*)-2,4-di(2-phenethyl)-4-carboxybutyryl]-3-aminopropionic acid isolated as the disodium salt melting at 260°–265° (dec); NMR (D$_2$O) δ 7.40 and 7.43 (s, 10H, Ar-H), 3.27 (m, 2H, NCH$_2$).

(b) N-[(R*,R*)-2,4-di(phenethyl-4-carboxybutyryl)]-3-aminopropionic acid isolated as the disodium salt melting at 205°–215° (dec); NMR (D$_2$O) δ 7.40 and 7.43 (s, 10H, Ar-H), 3.35 (m, 2H, NCH$_2$).

The starting materials are prepared as follows:

5.0 g of (R*,S*)-2,4-di(phenethyl)glutaric acid is refluxed in 50 ml of acetyl chloride for 3 hours, concentrated, diluted with toluene and evaporated to give a solid. The residue is recrystallized from cyclohexane:-toluene (3:1) to yield cis-2,4-di(phenethyl)glutaric anhydride melting at 79°–81°. The trans-2,4-di(phenethyl)glutaric anhydride is prepared similarly from the (R*,R*) diacid.

The mixture of isomers of 2,4-di-(phenethyl)glutaric acid are prepared following the general procedure described in *Acta Chem. Scand.* 1958, 12, 314. The reaction mixture is recrystallized from cyclohexane to yield (R*,S*)-2,4-di(phenethyl)glutaric acid melting at 129°–132°. The mother liquor is concentrated and the residue is recrystallized twice from cyclohexane:toluene (3:2) to yield (R*,R*)-2,4-di(phenethyl)glutaric acid melting at 95°–105°.

EXAMPLE 4

The suspension of 0.5 g of N-[(R*,R*)-2,4-dibenzyl-4-carboxybutyryl]-3-aminopropionic acid and 0.5 g of 5% Rh/C in 10 ml of ethanol and 10 ml of water is hydrogenated for 36 hours at 3 atmospheres pressure (50 psi). The mixture is filtered through celite and concentrated. The colorless oil is treated with 1.0N sodium hydroxide in methanol and concentrated to yield N-[(R*,R*)-2,4-di(cyclohexylmethyl)-4-carboxybutyryl]-3-aminopropionic acid as the disodium salt melting at 200°–210°

(dec); NMR (Me$_2$SO-d$_6$) δ 8.14 (m, 1H, N$\underline{H}$), 3.17 (m, 2H, NC$\underline{H}_2$).

EXAMPLE 5

(a) The solution of 1.5 g of 3-aminopropionic acid and 1.8 g of sodium carbonate in 30 ml of water at 0° is added to 2.2 g of 4-ethoxycarbonyl-(R*,R*)-2,4-dibenzylbutyryl chloride and the mixture is stirred at room temperature for 4 hours. The mixture is extracted with ether, and the aqueous layer is acidified with 2N hydrochloric acid. The acidic solution is extracted with ethyl acetate, washed with saturated brine, dried (magnesium sulfate), filtered and concentrated. The residue is recrystallized from ether to yield N-[4-ethoxycarbonyl-(R*,R*)-2,4-dibenzylbutyryl]-3-aminopropionic acid, melting at 84°-86°; NMR (CDCl$_3$) δ 10.5 (1H, CO$_2$$\underline{H}$), 6.1 (t, 1H, J=6 Hz, N$\underline{H}$), 4.1 (q, 2H, J=8 Hz, OC$\underline{H}_2$), 1.08 (t, 3H, J=8 Hz, C$\underline{H}_3$).

(b) Prepared similarly is N-[4-ethoxycarbonyl-(R*,R*)-2,4-dibenzylbutyryl]-4-aminobutyric acid obtained as a foam; NMR (CDCl$_3$) δ 9.8 (1H, CO$_2$$\underline{H}$), 7.3 (10H, Ar-$\underline{H}$), 5.68 (m, 1H, N$\underline{H}$), 4.07 (q, 2H, J=8 Hz, OC$\underline{H}_2$), 1.10 (t, 3H, J=8 Hz, C$\underline{H}_3$).

The starting material is prepared as follows: 4.0 g of trans-2,4-dibenzyl glutaric anhydride is refluxed in 40 ml of ethanol:toluene (3:2) overnight. The reaction mixture is concentrated to yield 4-ethoxycarbonyl-(R*,R*)-2,4-dibenzylbutyric acid as an oil. Oxalyl chloride (3.5 ml) is added to the solution of 4.5 g of 4-ethoxycarbonyl-(R*,R*)-2,4-dibenzylbutyric acid in 10 ml of methylene chloride. The mixture is stirred at room temperature overnight and evaporated to yield 4-ethoxycarbonyl-(R*,R*)-2,4-dibenzylbutyryl chloride, which is used as such without further purification.

EXAMPLE 6

The solution of 2.37 g of N-[4-ethoxycarbonyl-(R*,R*)-2,4-dibenzylbutyryl]-3-aminopropionic acid, 0.61 g of 3-pyridylcarbinol and 1.15 g of dicyclohexylcarbodiimide in 25 ml of methylene chloride is stirred at room temperature for two days. The solid is removed, and the filtrate is diluted with 150 ml of ether and extracted with 0.5N hydrochloric acid. The acidic aqueous layer is separated, basified and extracted with ethyl acetate. The organic layer is washed with saturated sodium chloride, dried over magnesium sulfate, filtered, concentrated and flash chromatographed on silica gel eluting with ethyl acetate:ethanol (9:1) to yield 3-pyridylmethyl N-[4-ethoxycarbonyl-(R*,R*)-2,4-dibenzylbutyryl]-3-aminopropionate as an oil; NMR (CDCl$_3$) δ 8.70 (m, 2H), 7.77 (m, 1H), 7.28 (m, 11H), 5.56 (t, 1H, J=7 Hz), 5.12 (s, 2H), 4.03 (q, 2H, J=8 Hz), 1.08 (t, 3H, J=8 Hz).

Treatment with ethanolic hydrogen chloride yields the hydrochloride salt.

EXAMPLE 7

Similarly to the procedure described in example 6, condensation of N-[4-ethoxycarbonyl-(R*,R*)-2,4-dibenzylbutyryl]-3-aminopropionic acid with morpholine in the presence of dicyclohexylcarbodiimide yields N-[N'-(4-ethoxycarbonyl-(R*,R*)-2,4-dibenzylbutyryl)-3-aminopropionyl]-morpholine as an oil; NMR (CDCl$_3$) δ 7.28 and 7.22 (s, 10H), 5.74 (t, 1H, J=7 Hz), 4.03 (q, 2H, J=8 Hz), 1.08 (t, 3H, J=8 Hz).

EXAMPLE 8

(a) To the solution of 150 mg of N-(4-methoxycarbonyl-2-phenethylbutyryl)-4-aminobutyric acid methyl ester in 3 ml of methanol is added 1.0 ml of 1N sodium hydroxide and stirred for 4 hours at room temperature. The mixture is acidified with 1.5 ml of 1N hydrochloric acid, and concentrated. The solid is collected and washed with water to yield N-(4-carboxy-2-phenethylbutyryl)-4-aminobutyric acid.

(b) Similarly prepared is N-(4-carboxy-4-phenethyl butyryl)-4-aminobutyric acid, from N-(4-methoxycarbonyl-4-phenethylbutyryl)-4-aminobutyric acid methyl ester.

The starting materials are prepared as follows: 1.90 g of 4-aminobutyric acid and 4.0 g of 2-phenethylglutaric anhydride (U.S. Pat. No. 4,374,847) in 20 ml of pyridine is heated at 80° overnight. The mixture is concentrated, the residue is dissolved in ethyl acetate and the solution is washed with 1N hydrochloric acid, saturated sodium chloride, dried over magnesium sulfate and concentrated to give an oil. The mixture of isomeric diacids is dissolved in 100 ml of methanol containing 5 drops of concentrated sulfuric acid and refluxed for 20 hours. The mixture is concentrated, diluted with methylene chloride, washed with saturated sodium bicarbonate, dried over magnesium sulfate, concentrated, chromatographed eluting with 40% ethyl acetate:hexane to yield N-(4-methoxycarbonyl-2-phenethylbutyryl)-4-aminobutyric acid methyl ester and N-(4-methoxycarbonyl-4-phenethylbutyryl)-4-aminobutyric acid methyl ester as individual isomers.

EXAMPLE 9

4-(Pivaloyloxymethoxycarbonyl)-2,4-(R*,R*)-dibenzylbutyryl chloride (1.2 g) in 10 ml of methylene chloride is added slowly to a solution of 1.15 g of benzyl 3-aminopropionate p-toluenesulfonic acid salt and 0.46 ml of triethylamine in 20 ml of methylene chloride. The reaction is stirred overnight at room temperature. The solution is washed with 2N hydrochloric acid, then with saturated sodium bicarbonate, dried over magnesium sulfate, filtered and concentrated to give N-[4-pivaloyloxymethoxycarbonyl-(R*,R*)-2,4-dibenzylbutyryl]-3-aminopropionic acid benzyl ester.

The starting material is prepared as follows:

A mixture of 4.0 g of 2,4-trans-dibenzylglutaric anhydride and 1.5 ml of benzyl alcohol in 15 ml of toluene is stirred at 80° for 16 hours to give 4-(benzyloxycarbonyl)-2,4-(R*,R*)-dibenzylbutyric acid.

The above acid (3.2 g) is treated with 3.8 ml of 2.1N potassium hydroxide. The solution is evaporated. Toluene (100 ml) is added and the mixture is evaporated to give the potassium 4-(benzyloxycarbonyl)-2,4-(R*,R*)-dibenzylbutyrate.

To chloromethyl pivalate (1.13 g) in 25 ml of acetone is added sodium iodide (1.11 g). The reaction is stirred at room temperature for 3 hours. The reaction mixture is filtered and the filtrate is evaporated. To the residue in 25 ml of dimethylformamide is added potassium 4-(benzyloxycarbonyl)-2,4-(R*,R*)-dibenzylbutyrate (3.3 g) in 25 ml of dimethylformamide. The reaction mixture is stirred at room temperature for 18 hours and then evaporated. The residue is dissolved in 150 ml of ether and washed with 3×50 ml of 10% aqueous sodium bicarbonate and 3×50 ml of saturated aqueous sodium chloride. The organic layer is dried over magnesium sulfate and evaporated to give pivaloyloxymethyl4-(benzyloxycarbonyl)-2,4-(R*,R*)-dibenzylbutyrate.

A solution of 2.5 g of pivaloyloxymethyl 4-(benzyloxycarbonyl)-2,4-(R*,R*)-dibenzylbutyrate in 75 ml of ethanol is hydrogenated at atmospheric pressure in the presence of 0.2 g of 5% palladium on carbon. The reaction is filtered and evaporated to give 4-(pivaloyloxymethoxycarbonyl)-2,4-(R*,R*)-dibenzylbutyric acid.

To 1.8 g of the above acid in 30 ml of methylene chloride at room temperature is added 1.2 ml of oxalyl chloride. The reaction is stirred at room temperature for 2.5 hours and then evaporated to give 4-(pivaloyloxymethoxycarbonyl)-2,4-(R*,R*)-dibenzylbutyryl chloride.

EXAMPLE 10

0.92 g of N-[4-pivaloyloxymethoxycarbonyl-2,4-(R*,R*)-dibenzylbutyryl]-3-aminopropionic acid benzyl ester in 20 ml of ethanol is hydrogenated at atmospheric pressure in the presence of 0.1 g of 5% palladium on carbon. The reaction is filtered and evaporated to give N-(4-pivaloyloxymethoxycarbonyl-2,4-(R*,R*)-dibenzylbutyryl)-3-aminopropionic acid.

EXAMPLE 11

(a) To the solution of 0.52 g of 3-amino-1-propanol in 10 ml of methylene chloride is added 0.5 g of 4-ethoxycarbonyl-2,4-(R*,R*)-dibenzylbutyryl chloride in 10 ml of methylene chloride. The mixture is stirred 10 minutes at room temperature. The reaction mixture is concentrated and diluted with ethyl acetate. The organic portions are washed with 1N hydrochloric acid, saturated sodium bicarbonate and saturated sodium chloride. The organic layer is dried over magnesium sulfate, filtered and concentrated to give N-[4-ethoxycarbonyl-2,4-(R*,R*)-dibenzylbutyryl]-3-amino-1-propanol as a colorless oil; NMR (CDCl$_3$) δ 7.31 and 7.28 (s, 10H, Ar-H), 5.82 (t, 1H, J=7 Hz, NH), 4.02 (q, 2H, J=8 Hz, OCH$_2$), 3.3–1.25 (m, 15H), 1.10 (t, 3H, J=8 Hz, CH$_3$).

(b) Similarly prepared from 3-aminopropionitrile is the N-[4-ethoxycarbonyl-2,4-(R*,R*)-dibenzylbutyryl]-3-aminopropio-nitrile; NMR (CDCl$_3$) δ 7.3 (m,10H), 4.0(q, 2H, J=8 Hz), 3.7–1.7 (multiplets).

EXAMPLE 12

(a) To a solution of 0.01 mole of 3-aminopropionic acid and 0.01 mole of (R*,R*)-4-ethoxycarbonyl-2,4-dibenzylbutyric acid in 40 ml of methylene chloride are added 0.01 mole of 1-(3-dimethylaminopropyl)-3-ethylcarbodiimide hydrochloride and 0.01 mole of triethylamine. The reaction mixture is stirred at room temperature for 3 days. Diethyl ether (250 ml) is added and the mixture is washed with 25 ml of water, 25 ml of 2N aqueous hydrochloric acid and 25 ml of saturated aqueous sodium bicarbonate solution. The organic layer is dried over magnesium sulfate and evaporated to give N-[4-ethoxycarbonyl-(R*,R*)-2,4-dibenzylbutyryl]-3-aminopropionic acid, the compound of example 5(a).

(b) To a solution of 0.012 mole of 1,1'-carbonyldiimidazole in 20 ml of methylene chloride at 0° is added a solution of 0.01 mole of (R*,R*)-4-ethoxycarbonyl-2,4-dibenzylbutyric acid in 20 ml of methylene chloride. After 1 hour 0.01 mole of 4-aminobutyric acid in 10 ml of pyridine is added dropwise over a period of 15 minutes. The reaction mixture is stirred at room temperature overnight. The reaction mixture is evaporated to dryness. The residue is dissolved in 75 ml of methylene chloride and washed with 2×25 ml of 2N aqueous hydrochloric acid. The organic layer is dried over magnesium sulfate and evaporated to give after recrystallization from ether N-[4-ethoxycarbonyl-(R*,R*)-2,4-dibenzylbutyryl]-4-aminobutyric acid, the compound of example 5b.

EXAMPLE 13

According to methods similar to those described in the previous examples are prepared the following compounds of formula III wherein A represents ethylene or propylene, R$_1$' and R$_2$' are identical, and R$_4$ represents hydroxy, as the threo isomers.

| Compound | R$_1$' and R$_2$' | R$_3$ |
|---|---|---|
| 13/1 | benzyl | l-bornyloxycarbonylmethoxy |
| 13/2 | benzyl | 3-phthalidoxy |
| 13/3 | benzyl | 1-(ethoxycarbonyloxy)-ethoxy |
| 13/4 | benzyl | 1-(ethoxycarbonyl)-ethoxy |
| 13/5 | p-chlorobenzyl | hydroxy |
| 13/6 | p-cyanobenzyl | hydroxy |
| 13/7 | p-trifluoromethylbenzyl | hydroxy |
| 13/8 | p-methylbenzyl | hydroxy |
| 13/9 | benzyl | 3-pyridylmethoxy |
| 13/10 | benzyl | amino |
| 13/11 | benzyl | dodecylamino |
| 13/12 | benzyl | hexadecyloxy |
| 13/13 | benzyl | cholest-5-en-3β-oxy |
| 13/14 | methyl | ethoxy |

Starting materials for compounds 13/1 through 13/4 are l-bornyl iodoacetate, 3-bromophthalide, 1-chloroethyl ethyl carbonate, and ethyl lactate respectively.

Starting material for compound 13/13 is cholesterol.

EXAMPLE 14

According to methods similar to those described in the previous examples are prepared the following compounds of formula II.

| Compound | R$_1$ and R$_2$ | A |
|---|---|---|
| 14/1 | benzyl | —CH(CH$_3$)—CH$_2$— |
| 14/2 | 2-(3-thienyl)-ethyl | —CH$_2$CH$_2$— |
| 14/3 | 2-(2-thienyl)-ethyl | —CH$_2$CH$_2$CH$_2$— |
| 14/4 | 3-pyridylmethyl | —CH$_2$CH$_2$— |
| 14/5 | 2-(2-naphthyl)-ethyl | —CH$_2$CH$_2$— |
| 14/6 | 4-biphenylmethyl | —CH$_2$CH$_2$CH$_2$— |
| 14/7 | 2-biphenylmethyl | —CH$_2$CH$_2$CH$_2$— |
| 14/8 | benzyl | 1,4-cyclohexylene |
| 14/9 | phenethyl | 1,3-cyclohexylene |
| 14/10 | cyclopentylmethyl | —CH$_2$CH$_2$CH$_2$— |
| 14/11 | benzyl | —CH$_2$—CH(p-ClC$_6$H$_4$)—CH$_2$— |

Compound 14/11 is isolated as the disodium salt, melting at 138–149°.

EXAMPLE 15

Preparation of an injectable formulation containing 25 mg of the active ingredient per 5 ml of solution:

| Formula | |
|---|---|
| N-(R*,R*)-2,4-Dibenzyl-4-carboxybutyryl)-3-aminopropionic acid | 25.0 g |

| Formula | |
|---|---|
| Sodium bicarbonate | 5.5 g |
| Propylparaben | 1.0 g |
| Water for injection q.s. | 5000.0 ml |

The active ingredient, sodium bicarbonate and preservative are dissolved in 3500 ml of water for injection and the solution is diluted to 5000 ml. The solution is filtered through a sterile filter and filled into injection vials under sterile conditions each vial containing 5 ml of the solution.

EXAMPLE 16

Preparation of 10,000 capsules each containing 20 mg of the active ingredient.

| Formula | |
|---|---|
| N-[4-Ethoxycarbonyl(R*,R*)-2,4-dibenzylbutyryl]-3-aminopropionic acid | 200.00 g |
| Lactose | 1,790.0 g |
| Magnesium stearate | 10.0 g |

PROCEDURE

The powders are passed through a screen with openings of 0.6 mm. Then the drug substance is placed in a suitable mixer and mixed with the lactose and magnesium stearate until homogeneous. No. 3 capsules are filled with 200 mg using a capsule filling machine.

Analogously, injectable formulations or capsules are prepared from the remaining compounds of the invention, e.g., those illustrated by the examples herein.

EXAMPLE 17

According to methods similar to those described in the previous examples are prepared the following compounds of formula IVa (of S,S-configuration) wherein m and n represent the integer 1, p is the integer 2, and $R_5$ and $R_6$ represent hydrogen. Unless otherwise indicated $[\alpha]_D^{25}$ is measured in methanol (c=1.0).

| Compound | $R_3'$ and $R_4'$ | m.p. | $[\alpha]_D^{25}$ |
|---|---|---|---|
| 17/1 | $R_3'$ = 1,2:5,6-di-O-isopropylidene-D-glucofuranos-3-yloxy; $R_4'$ = OH. | 68–71° | +1.0 |
| 17/2 | $R_3'$ = 1,2:3,4-di-O-isopropylidene D-galactopyranos-6-yloxy; $R_4'$-OH. | 63–65° | −4.7° |
| 17/3 | $R_3'$ = 2,3-O-isopropylidene-D-ribono-(1,4-lactone)-5-yloxy; $R_4'$ = OH. | 150–152° | +2.4° |
| 17/4 | $R_3'$ and $R_4'$ = cholest-5-en-3β-oxy. | 72–75° | −20.8° (CHCl₃) |
| 17/5 | $R_3'$ = (2,2-dimethyl-1,3-dioxolan-4-yl)-methoxy; $R_4'$ = OH; sodium salt. | 63–66° | +17.3° |
| 17/6 | $R_3'$ = OH; $R_4'$ = 2,3-O-isopropylidene-D-ribono-(1,4-lactone)-5-yloxy. | 106–109° | −1.0° |
| 17/7 | $D_3'$ = OH; $R_4'$ = 2,3:5,6-di-O-cyclohexylidene-D-mannofuranos-1-yloxy; sodium salt. | 90–97° | +27.6° |
| 17/8 | $R_3'$ = OH; $R_4'$ = 2,3-O-cyclohexylidene-D-ribono-(1,4-lactone)-5-yloxy; sodium salt. | 109–112° | +9.8° |
| 17/9 | $R_3'$ = OH; $R_4'$ = 1,2:3,4-di-O-isopropylidene-D-galactopyranos-6-yloxy; sodium salt. | 70–75° | −12.4° |
| 17/10 | $R_3'$ = OH; $R_4'$ = 1,2:5,6-di-O-isopropylidene-D-glucofuranos-3-yloxy. | 67–70° | +11° |
| 17/11 | $R_3'$ = OH; $R_4'$ = 1-methyl-2,3-O-isopropylidene-β-D-ribofuranos-5-yloxy; sodium salt. | 40–50° | −11.8° |
| 17/12 | $R_3'$ = n-butoxy; $R_4'$ = 4-pyridylmethoxy. | IR 1729 cm-1 | +19.3° |
| 17/13 | $R_3'$ = 2,3-O-isopropylidene-D-ribono-(1,-4-lactone)-5-yloxy; $R_4'$ = 4-pyridylmethoxy | 153–155° | +9.3° |
| 17/14 | $R_3'$ = dimethylaminoethylamino; $R_4'$ = 1,2:5,6-di-O-isopropylidene-D-glucofuranos-3-yloxy. | 85–89° | +35° |
| 17/15 | $R_3'$ = OH; $R_4'$ = cholest-5-en-3β-oxy. | 152–154° | +9.6° |
| 17/16 | $R_4'$ = OH; $R_3'$ = cholest-5-en-3β-oxy. | 134–139° | +10° |
| 17/17 | $R_4'$ = OH; $R_3'$ = ethoxy. | 79–81° | +18° |
| 17/18 | $R_4'$ = OH; $R_3'$ = pivaloyloxymethoxy; sodium salt. | 97–104° | — |
| 17/19 | $R_3'$ = dimethylaminoethylamino; $R_4'$ = cholest-5-en-3β-oxy. | 142–146° | +33.4° |
| 17/20 | $R_3'$ = n-butoxy; $R_4'$ = 2,3-O-isopropylidene-D-ribono-(1,4-lactone)-5-yloxy. | (oil) | −6.21° |
| 17/21 | $R_3'$ = 1,2:3,4-di-O-isopropylidene-D-galactopyranos-6-yloxy; $R_4'$ = 4-pyridylmethoxy. | 41–44° | + 9.2°(c = 0.5) |
| 17/22 | $R_3'$ = OH; $R_4'$ = 1,2-O-isopropylidene-D-glucofuranos-3-yloxy; sodium salt. | 70–75° | +5.1° |
| 17/23 | $R_3'$ = OH; $R_4'$ = 2,3:4,6-di-O-isopropylidene-α-L-sorbofuranos-1-yloxy; sodium salt. | 71–76° | +1.3° |
| 17/24 | $R_3'$ = ethyoxy; $R_4'$ = 1,2:5,6-di-O-isopropylidene-D-glucofuranos-3-yloxy | (oil) | +5.4° |

-continued

| Compound | R₃' and R₄' | m.p. | $[\alpha]_D^{25}$ |
|---|---|---|---|
| 17/25 | R₃' = ethoxy; R₄' = 2,3-O-benzylidene-D-ribono(1,4-lactone)-5-yloxy | 37-40° | -13.2° |
| 17/26 | R₃' = 2,3-O-benzylidene-D-ribono(1,4-lactone)-5-yloxy; R₄' = OH | 144-147° | +0.4° |
| 17/27 | R₃' = OH; R₄' = D-ribono(1,4-lactone)-5-yloxy. | 47-50° | +27.0° |
| 17/28 | R₃' = OH; R₄' = 1,2:5,6-di-O-isopropylidene-D-allofuranos-3-yloxy; sodium salt. | 84-88° | +71.7° |
| 17/29 | R₃' = OH; R₄' = 1,2-O-isopropylidene-5,6-bis-O-acetyl-D-glucofuranos-3-yloxy; sodium salt. | 95-100° | +19.0° |
| 17/30 | R₃' = OH; R₄' = 1,2:5,6-di-O-cyclohexylidene-D-glucofuranos-3-yloxy. | 107-110° | +8.4° |
| 17/31 | R₃' = 1,2-O-isopropylidene-D-glucofuranos-3-yloxy; R₄' = OH. | 90-96° | +1.5° |
| 17/32 | R₃' = 3-phthalidoxy; R₄' = OH | 46-49° | +14.0° |
| 17/33 | R₃' = OH, R₄' = 2,3-O-benzylidene-D-ribono(1,4-lactone)-5-yloxy. | 64-67° | -9.0° |

ILLUSTRATIVE PROCEDURES (a) The compound of Example 17/21 is prepared as follows:

To the solution of 0.85 g of 4-[1,2:3,4-di-O-isopropylidene-D-galactopyranos-6-yloxy-carbonyl]-(S,S)-2,4-dibenzylbutyric acid and 0.4 g of 4-pyridylmethyl 3-amino-propionate dihydrochloride salt (prepared as described in *Aust. J. Chem.*, 1987, 31, 1865) and 0.32 g of triethylamine in 5 ml methylene chloride is added 0.31 g of 1-(3-dimethylaminopropyl)-3-ethylacarbodiimide hydrochloride. The mixture is stirred overnight, diluted with ethyl acetate, washed with saturated sodium bicarbonate, water, dried (Na₂SO₄), filtered and concentrated. The residue is flash chromatographed on silica gel eluting with ethyl acetate to give 4-pyridylmethyl N-[4-(1,2,3,4-di-O-isopropylidene-D-galactopyranos-6-yloxy-carbonyl)-(S,S)-2,4-dibenzylbutyryl]-3-aminopropionate melting at 41°-44° ; $[\alpha]_D^{25} = +9.2°$ (c=0.5 in methanol).

(b) The starting material for compound of Example 17/1 is prepared as follows:

To the solution of 1.6 g of N-[(S,S)-2,4-dibenzyl-4-carboxybutyryl]-3-aminopropionic acid benzyl ester and 0.88 g of diacetone-D-glucose (1,2:5,6-diisopropylidene-D-glucose) in 20 ml of methylene choride is added 0.74 g of 1-(3-dimethylaminopropyl)-3-ethylcarbodiimide hydrochloride and 0.41 g of 4-dimethylaminopyridine. The mixture is stirred at room temperature overnight, diluted with ethyl acetate and washed with 1N hydrochloric acid, water, saturated sodium bicarbonate, water, dried (Na₂SO₄), filtered and concentrated.

The residue is flash chromatographed on silica gel eluting with ethyl acetate: methylene chloride (1:4) to give N-{4[(4,2:5,6-di-O-isopropylidene-D-glucofuranos-3-yloxy)-carbonyl]-2,4-(S,S)-dibenxylbutyryl}-3-amino-propionic acid benzyl ester as a colorless foam.

(c) The starting material for compound of Example 17/2 is prepared as follows:

The solution of 1 g of (S,S)-2,4-dibenzylglutaric anhydride and 1.06 g of 1,2,3,4-di-O-isopropylidene-D-galactopyranose in 10 ml of toluene is refluxed overnight. The solution is diluted with toluene, washed with water, dried (Na₂SO₄), filtered, and concentrated to give 4-[1,2:3,4-di-O-isopropylidene-D-galactopyranos-6-yloxy-carbonyl]-(S,S)-2,4-dibenzylbutyric acid as a viscous oil.

To the solution of 0.85g of 4-(1,2:3,4-di-O-isopropylidene-D-galactopyranos-6-yloxy-carbonyl)-(S,S)-2,4-dibenzylbutyric acid, 0.56 g of 3-aminopropionic acid benzyl ester p-toluenesulfonate and 0.16 g of triethylamine in 15 ml of methylene chloride is added 0.31 g of 1-(3-dimethylaminopropyl)-3-ethylcarbodiimide hydrochloride. The solution is stirred at room temperature overnight. The solution is diluted with ethyl acetate, washed with 1N hydrochloric acid, water, saturated sodium bicarbonate, water, dried (Na₂SO₄), filtered and concentrated. The residue is flash chromatographed on silica gel eluting with ethyl acetate: methylene chloride (1:4) giving N-[4(1,2:3,4-di-O-isopropylidene-D-galactopyranos-6-yloxy-carbonyl)-(S,S)-2,4-dibenzylbutyryl]-3-aminopropionic acid benzyl ester as a glass.

The cited esters, either as starting materials or final products, are prepared using the alcohols corresponding to R₃' and/or R₄', which are either commercially available, known in the literature or prepared according to known methods, e.g.

(a) 2,3:5,6-di-O-cyclohexylidene-α-D-mannofuranose, J. Chem. Soc. 853 (1959);
(b) 2,3-O-isopropylidene-D-ribono-1,4-lactone, Can. J. Chem. 1720 (1958);
(c) 2,3:4,6-di-O-isopropylidene-α-L-sorbofuranose, Biochemistry 26, 201 (1971);
(d) 1-methyl-2,3-O-isopropylidene-D-ribofuranoside;
(e) 2,2-dimethyl-1,3-dioxolane-4-methanol;
(f) 1,2:5,6-di-O-isopropylidene-D-glucofuranose;
(g) 1,2:5,6-di-O-isopropylideneα-D-allofuranose;
(h) 1,2:3,4-di-O-isopropylidene-D-galactopyranose;
(i) 1,2-O-isopropylidene-D-glucofuranose;
(j) chlolest-5-en-3β-ol;
(k) phthalide

EXAMPLE 18

According to procedures essentialy as described in previous examples are prepared:

(a) N-[(R*,R*)-2,4di(p-methylbenzyl)-4-carboxybutyryl]-3-aminopropionic acid, isolated as the disodium salt, melting at 290°-295° dec (see Example 13/8).

The starting material racemic (R*,R*)-2,4-di(p-methylbenzyl)-glutaric acid is prepared according to the procedure described in Example 1 for 2,4-dibenzyl-glutaric acid using corresponding p-methyl substituted starting materials.

(b) {N-[(S,S)-2,4-dibenzyl-4-ethoxycarbonylbutyryl]-3-amino-}-(N-dodecyl)-propionamide, melting at 72°-77°.
(c) N-(R*,R*-2,4-dibenzyl-4-carboxybutyryl)-cis-2-aminocyclohexanecarboxylic acid, m.p. 145°-160°.
(d) N-(S,S-2,4-dimethyl-4-carboxybutyryl)-3-aminopropionic acid disodium salt, m.p. 125°-129°.

EXAMPLE 19

According to procedures essentially as described in the previous examples are prepared the following compounds of formula IVa (of S,S-configuration) wherein m and n represent the integer 1, p is 3, $R_5$ and $R_6$ represent hydrogen, and (a) $R_3'$=hydroxy; $R_4'$=2,3-O-isopropylidene-D-ribono-(1,4-lactone)-5-yloxy, isolated as the sodium salt, melting at 94°-104° dec; $[\alpha]_D^{25}$=+5.9° (c=1.0 in methanol);
(b) $R_3'$=OH; $R_4'$=D-ribono-(1,4 lactone)-5-yloxy; $[\alpha]_D^{25}$=+15.2° (c=1.0 in methanol) isolated as the sodium salt;
(c) $R_3'$=ethoxy; $R_4'$=2,3-O-benzylidene-D-ribono-(1,4-lactone)-5-yloxy; p0 (d) $R_3'$=OH; $R_4'$=2,3-O-benzylidene-D-ribono-(1,4-lactone)-5-yloxy; m.p. 59°-62°; $[\alpha]_D^{25}$=−8.9° (c=0.5 in methanol);
(e) $R_3'$=OH; $R_4'$=1,2:3,4-di-O-isopropylidene-D-galactopyranos-6-yloxy; m.p. 62°-68°; $[\alpha]_D^{25}$=−11.8° (c=1.0 in methanol), isolated as the sodium salt;
(f) $R_3'$=OH; $R_4'$=2,3-O-cyclohexylidene-D-ribono-(1,4-lactone)-5-yloxy, isolated as the sodium salt, melting at 99°-104°; $[\alpha]_D^{25}$=+11.8 (C=1.0 in methanol);
(g) $R_3'$=OH; $R_4'$=1,2:5,6-di-O-cyclohexylidene-D-glucofuranos-3-yloxy; m.p. 58°-64°; $[\alpha]_D^{25}$=+5.5° (C=1.0 in methanol);
(h) $R_3'$=OH; $R_4'$=1,2:5,6-di-O-isopropylidene-D-glucofuranos-3-yloxy; m.p 60°-64°; $[\alpha]_D^{25}$=+1.0° (C=1.0 in methanol), isolated as the sodium salt;
(i) $R_3'$=ethoxy; $R_4'$=2,3-O-isopropylidene-D-ribono-(1,4-lactone)-5-yloxy; oil; $[\alpha]_D^{25}$=−8.6° (C=1.0 in methanol).

EXAMPLE 20

The solution of 300 mg of N-[(S,S)-2,4-dibenzyl-4-carboxybutyryl]-3-aminopropionic acid 1,2,5,6-di-O-isopropylidene-D-glucofuranos-3-yl ester (compound of Example 17/10) in 9 ml of 80% aqueous acetic acid is stirred at room temperature for 24 hours. The mixture is concentrated. Residual acetic acid is removed by addition of toluene and concentrating the solution; a colorless oil is obtained. The resulting N-[(S,S)-2,4-dibenzyl-4-carboxybutyryl]-3-aminopropionic acid 1,2-O-isopropylidene-D-glucofuranos-3-yl ester is isolated as the sodium slat melting at 70°-75° (compound of Example 17/22).

What is claimed is:
1. A compound of the formula

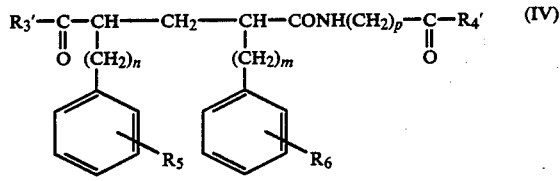

wherein m and n independently represent an integer from 1 to 4; p represents an integer from 2 to 4; $R_3'$ and $R_4'$ independently represent hydroxy, ($C_1$-$C_{20}$)-alkoxy, pivaloyloxymethoxy, bornyloxycarbonylmethoxy, benzyloxy, pyridylmethoxy or 1-(lower alkoxycarbonyloxy)-lower alkoxy; $R_5$ and $R_6$ independently represent hydrogen, halogen, hydroxy, lower alkoxy, lower alkyl or trifluoromethyl; or a pharmaceutically acceptable salt thereof.

2. A compound according to claim 1 wherein m, n, p, $R_5$ and $R_6$ are as defined therein; both of $R_3'$ and $R_4'$ represent alkoxy of 1 to 4 carbon atoms, 3-pyridylmethoxy, benzyloxy, pivaloyloxymethoxy, bornyloxycarbonylmethoxy, 1-(ethoxycarbonyloxy)-ethoxy; or one of $R_3'$ and $R_4'$ is as defined above and the other represents hydroxy; or a pharmaceutically acceptable salt thereof.

3. A compound according to claim 1 wherein m and n represent the integer 1 or 2; p represents the integer 2 or 3; $R_3'$ and $R_4'$ independently represent hydroxy, lower alkoxy, pivaloyloxymethoxy, pyridylmethoxy or benzyloxy; $R_5$ and $R_6$ have meaning as defined in said claim; or a pharmaceutically acceptable salt.

4. A compound according to claim 1 as the threo diastereoisomer or a pharmaceutically acceptable salt.

5. A compound according to claim 1 of the formula

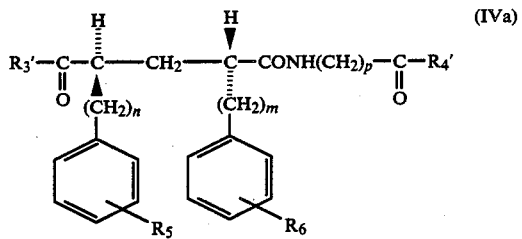

or a pharmaceutically acceptable salt thereof.

6. A compound of claim 1 being N-(2,4-dibenzyl-4-carboxybutyryl)-4-aminobutyric acid or N-(2,4-dibenzyl-4-carboxybutyryl)-3-aminopropionic acid, a steroisomer thereof or a pharmaceutically acceptable salt thereof.

7. N-[(R*,R*)-2,4-di-benzyl-4-carboxybutyryl]-3-aminopropionic acid or N-[(R*,R*)-2,4-dibenzyl-4-carboxybutyryl]-4-aminobutyric acid; a pharmaceutically acceptable mono- or diester derivative thereof selected from straight chain or branched $C_1$-$C_{20}$-alkyl, pivaloyloxymethyl, bornyloxycarbonylmethyl, benzyl, pyridylmethyl and 1-(lower alkoxycarbonyloxy)-lower alkyl ester; the S,S-antipode of a said compound; or a pharmaceutically acceptable salt thereof.

8. A compound of claim 7 being N-[(R*,R*)-4-ethoxycarbonyl-2,4-dibenzylbutyryl]-3aminopropionic acid or a pharmaceutically acceptable salt thereof.

9. A compound of claim 7 being 3-pyridylmethyl N-[(R*,R*)-4-ethoxycarbonyl-2,4-dibenzylbutyryl]-3-aminopropionate, or a pharmaceutically acceptable acid addition salt thereof.

10. A compound according to claim 5 wherein m and n represent the integer 1 and p represents the integer 2 or 3; $R_3'$, $R_4'$, $R_5$ and $R_6$ have meaning as defined in said claim or a pharmaceutically acceptable salt thereof.

11. An enkephalinase inhibiting pharmaceutical composition for administration to mammals comprising an effective amount of a compound of claim 1 in combination with one or more pharmaceutically acceptable carriers.

12. A method of inhibiting enkephalinase activity in mammals which comprises admininistering to a mannal in need thereof an effective amount of a compound of claim 1.

13. A method of inhibiting enkephalinase activity in mammals which comprises administering to a mannal in need thereof an effective amount of a compound of claim 7.

14. An enkephalinase inhibiting pharmaceutical composition for administration to mammals comprising an effective amount of a compound of claim 6 in combination with a pharmaceutically acceptable carrier.

* * * * *